(12) United States Patent
Trupp et al.

(10) Patent No.: US 11,167,981 B2
(45) Date of Patent: Nov. 9, 2021

(54) SEMICONDUCTOR DEVICE AND METHOD OF PRODUCING A SEMICONDUCTOR DEVICE

(71) Applicant: Fraunhofer-Gesellschaft zur Foerderung der angewandten Forschung e.V., Munich (DE)

(72) Inventors: Sabine Trupp, Saalfeld (DE); Michael Henfling, Munich (DE); Karl Neumeier, Taufkirchen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 16/669,411

(22) Filed: Oct. 30, 2019

(65) Prior Publication Data

US 2020/0062586 A1 Feb. 27, 2020

Related U.S. Application Data

(63) Continuation of application No. 15/875,635, filed on Jan. 19, 2018, now Pat. No. 10,519,034.

(30) Foreign Application Priority Data

Jan. 20, 2017 (DE) .................... 10 2017 200 952.7

(51) Int. Cl.
*B81B 3/00* (2006.01)
*B81C 1/00* (2006.01)
*G01N 33/00* (2006.01)

(52) U.S. Cl.
CPC ........ *B81C 1/00206* (2013.01); *B81B 3/0083* (2013.01); *B81B 3/0089* (2013.01); *B81B 2201/0214* (2013.01); *B81B 2201/0292* (2013.01); *B81C 2201/016* (2013.01); *B81C 2201/0114* (2013.01); *B81C 2201/0115* (2013.01); *G01N 33/0027* (2013.01); *H01L 2924/13072* (2013.01)

(58) Field of Classification Search
None
See application file for complete search history.

(56) References Cited

U.S. PATENT DOCUMENTS

| | | | |
|---|---|---|---|
| 2005/0019799 A1* | 1/2005 | Grasso | G01N 33/54373 435/6.11 |
| 2007/0014754 A1 | 1/2007 | Denkewicz et al. | |
| 2007/0087564 A1 | 4/2007 | Speakman | |

(Continued)

OTHER PUBLICATIONS

Altmaier, Stephan, "Modification and functionalization of ordered mesostrukturierter materials—Part 1 of 6", Thesis, Fachbereich Chemie der Universität Hannover, 2003, 2003.

(Continued)

*Primary Examiner* — Reema Patel
(74) *Attorney, Agent, or Firm* — Perkins Coie LLP; Michael A. Glenn

(57) ABSTRACT

A method of producing a semiconductor device includes providing a carrier structure having a semiconductor substrate; applying or introducing a precursor substance onto or into the carrier structure, treating the precursor substance for producing a porous matrix structure; introducing a functionalization substance into the porous matrix structure.

11 Claims, 18 Drawing Sheets

(56) References Cited

U.S. PATENT DOCUMENTS

| | | |
|---|---|---|
| 2010/0310422 A1 | 12/2010 | Grasso et al. |
| 2013/0192993 A1 | 8/2013 | Mardilovich et al. |
| 2016/0153104 A1 | 6/2016 | Yamashita |
| 2016/0251516 A1 | 9/2016 | Sorensen et al. |
| 2018/0133679 A1* | 5/2018 | Malcolm ............ B81C 1/00896 |

OTHER PUBLICATIONS

Altmaier, Stephan, "Modification and functionalization of ordered mesostrukturierter materials—Part 2 of 6", Thesis, Fachbereich Chemie der Universität Hannover, 2003, 2003.

Altmaier, Stephan, "Modification and functionalization of ordered mesostrukturierter materials—Part 3 of 6", Thesis, Fachbereich Chemie der Universität Hannover, 2003, 2003.

Altmaier, Stephan, "Modification and functionalization of ordered mesostrukturierter materials—Part 4 of 6", Thesis, Fachbereich Chemie der Universität Hannover, 2003, 2003.

Altmaier, Stephan, "Modification and functionalization of ordered mesostrukturierter materials—Part 5 of 6", Thesis, Fachbereich Chemie der Universitat Hannover, 2003, 2003.

Altmaier, Stephan, "Modification and functionalization of ordered mesostrukturierter materials—Part 6 of 6", Thesis, Fachbereich Chemie der Universität Hannover, 2003, 2003.

Andrieu-Brunsen, Annette, "Application of functional polymers in porous structures for transport control, switchable Nanokanale", labor&more, 2015, URL: http://www.laborundmore.com/archive/977373/Anwendung-von-funktionalen-Polymeren-in-poroesen-Strukturen-zur-Transportkontrolle.html., 2015.

Papez, Vitezslav et al., "Deposition of the chemically sensitive polymer layer on SGFET gate by laser-induced chemical-vapour polymerization", Sensors and Actuators B: Chemical, 40 (2-3), 143-45, 1997, 1997, pp. 143-145.

Wilbertz, CH. et al., "Suspended-Gate-and Lundstrom-FET integrated on a CMOS-chip", Sensors and Actuators A: Physical, 123-124, 2-6, 2005, 2005, pp. 2-6.

* cited by examiner

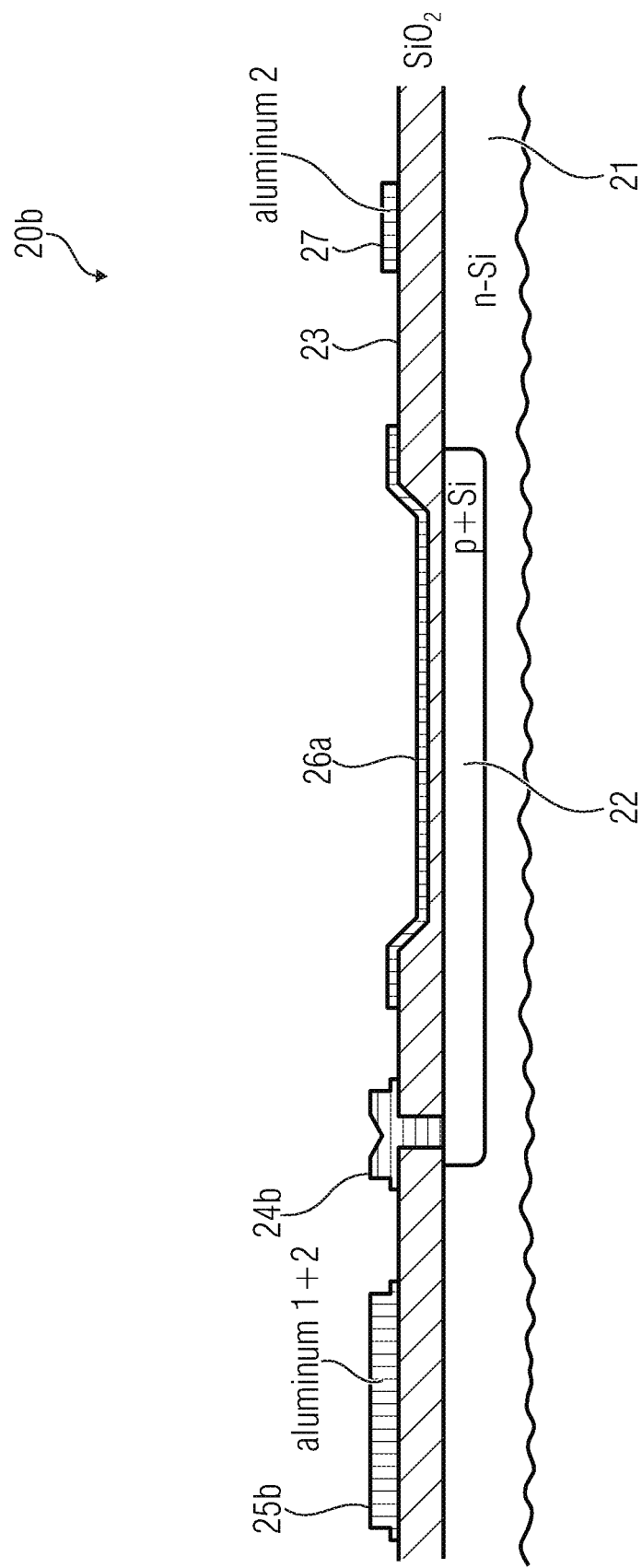

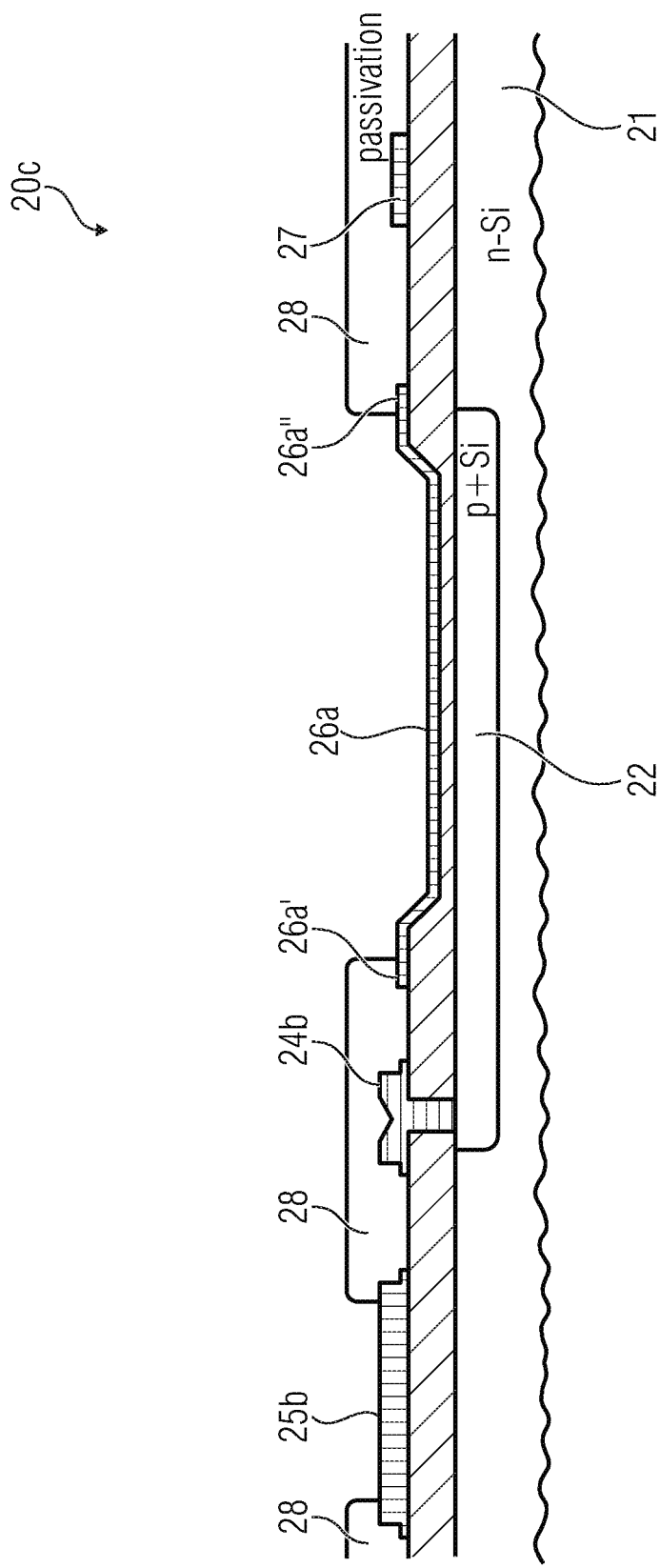

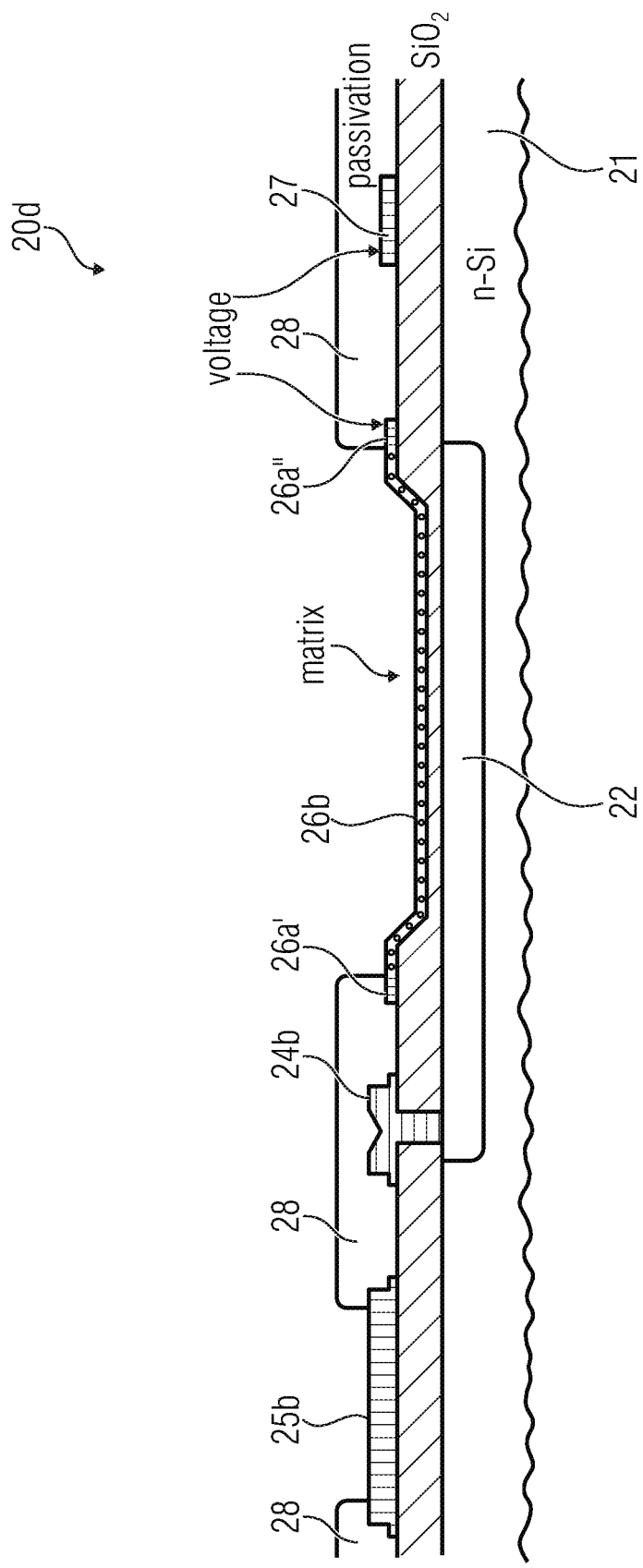

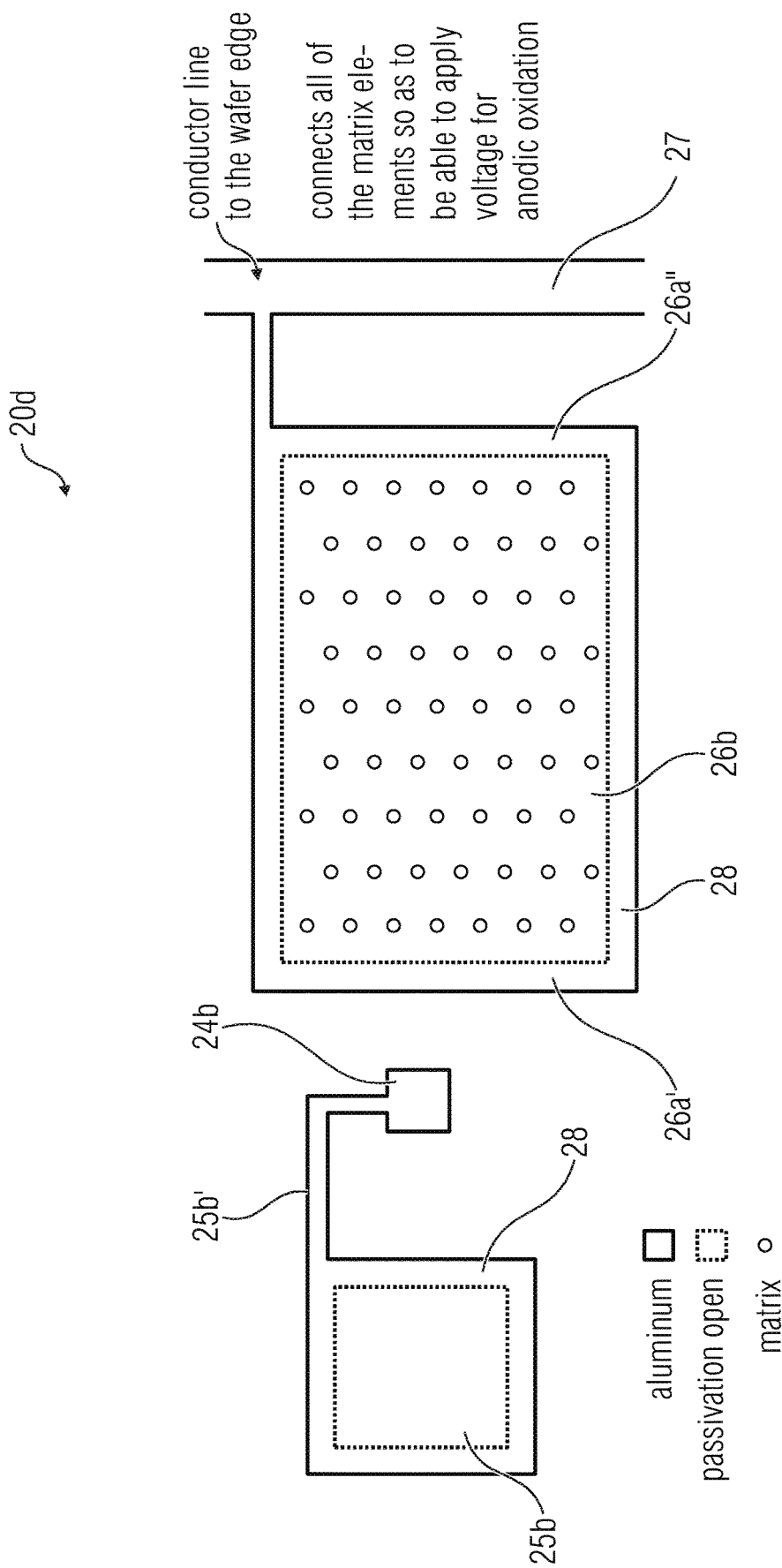

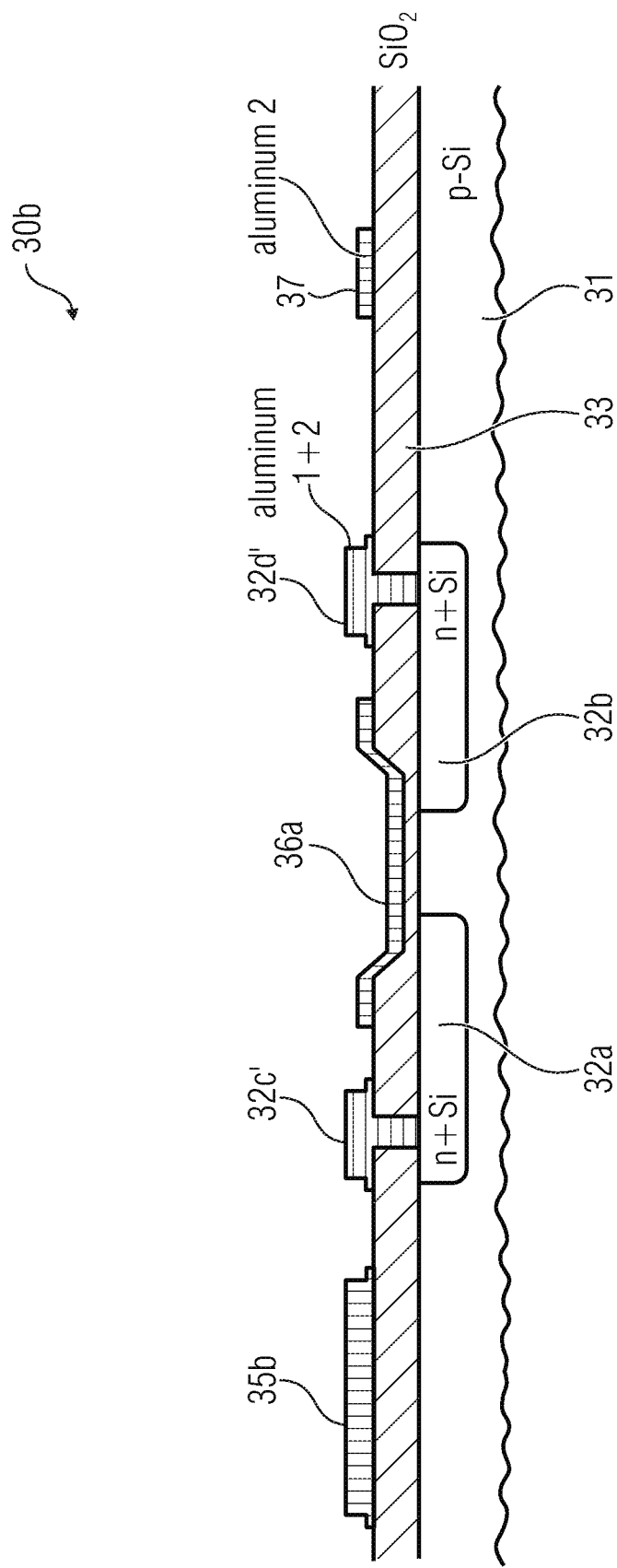

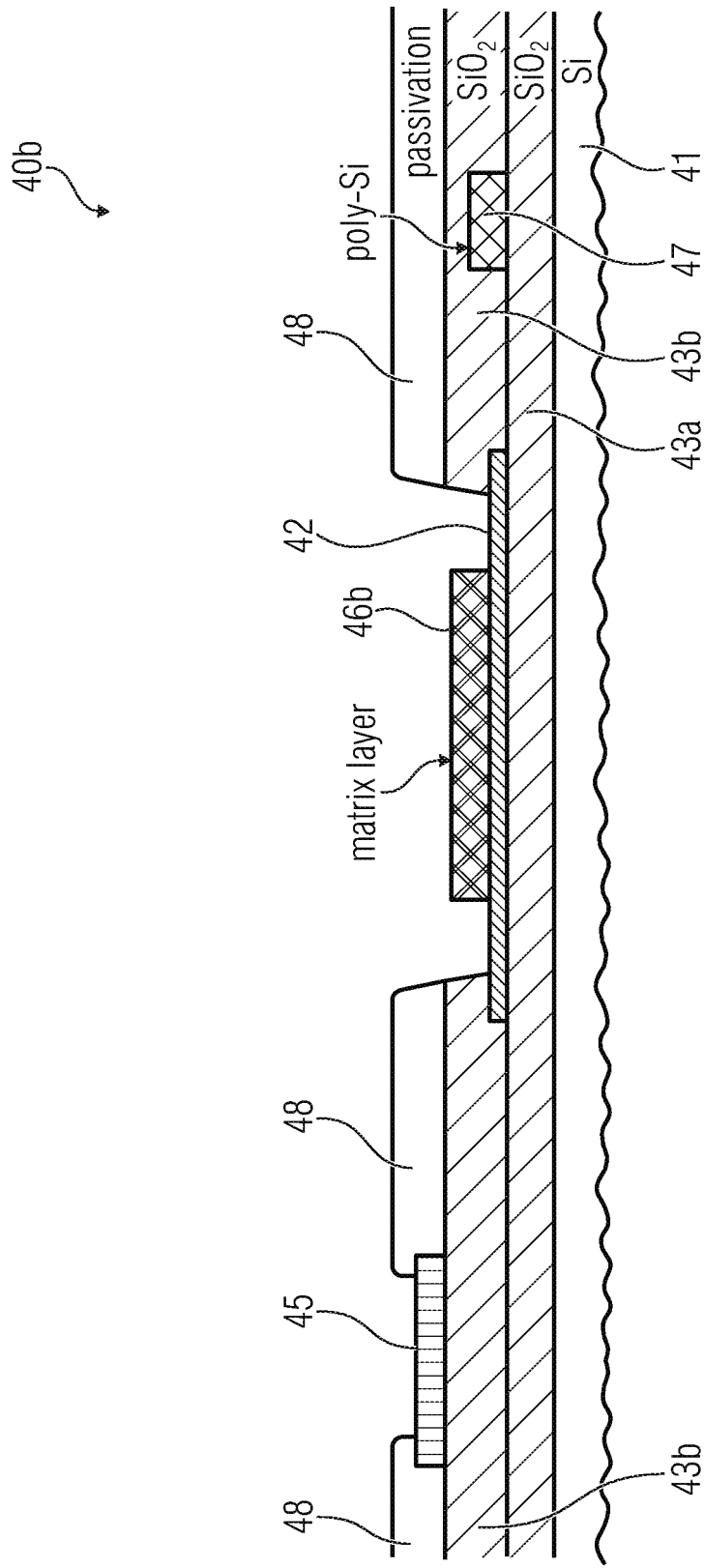

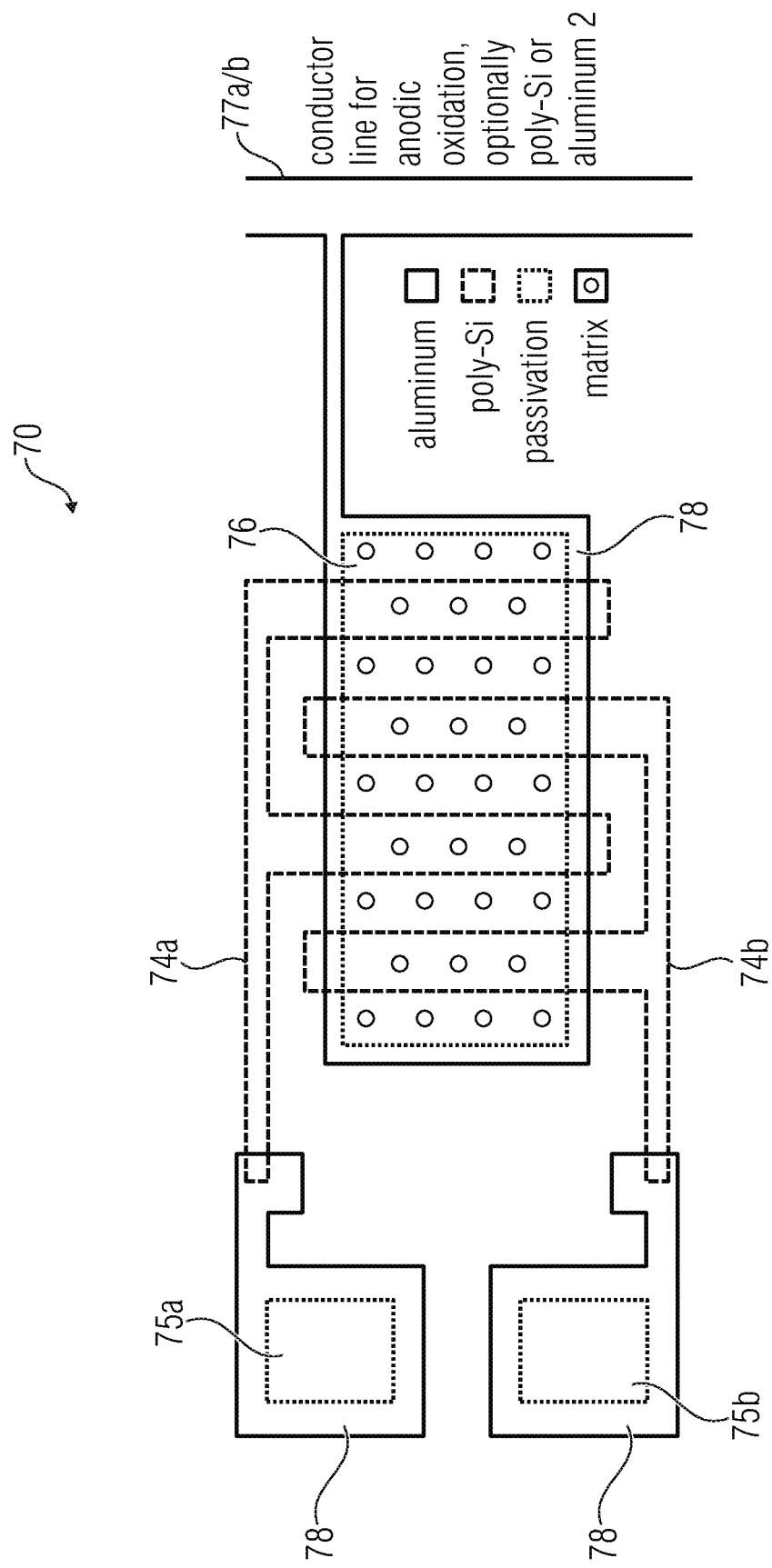

SEMICONDUCTOR DEVICE AND METHOD OF PRODUCING A SEMICONDUCTOR DEVICE

CROSS-REFERENCE TO RELATED APPLICATION

This application is a continuation to U.S. patent application Ser. No. 15/875,635 filed Jan. 19, 2018, which claims priority from German Patent Application No. DE 10 2017 200 952.7, which was filed on Jan. 20, 2017, and is incorporated herein in its entirety by reference.

The present invention relates to a method of producing a semiconductor device and to a semiconductor device produced in accordance with said method.

BACKGROUND OF THE INVENTION

For producing new components and systems, for example for sensor-technology applications, it may be useful to be able to apply a broad selection of reactive materials, e.g. indicator materials, onto components, or to introduce them into the systems, in a stable manner without restricting their functions, e.g. indicator functions. Common methods of coating with functionalized materials, e.g. indicator materials, are subject to various limitations (process temperature, e.g. when embedded in polymers as carrier matrices for painting and printing processes). In addition, many methods nevertheless provide no long-term stable, chemically or mechanically stable solutions. As a result, only a limited selection of functionalized coatings, e.g. indicator coatings, are currently available for developing suitable semiconductor components with functionalized materials, e.g. for sensor-technology applications.

Therefore, there is a need for a concept of improved introduction of functionalization substances into semiconductor devices.

SUMMARY

According to an embodiment, a method of producing a semiconductor device may have the steps of: providing a carrier structure including a semiconductor substrate; applying or introducing a precursor substance onto or into the carrier structure; treating the precursor substance for producing a porous matrix structure; introducing a functionalization substance into the porous matrix structure.

According to another embodiment, a semiconductor device may have: a semiconductor substrate; wherein the semiconductor substrate includes a plurality of integrated circuit configurations; wherein the integrated circuit configurations include a layer having a porous matrix structure, wherein a functionalization substance is introduced into the porous matrix structure.

Embodiments in accordance with the invention provide a method of producing a semiconductor device, comprising providing a carrier structure comprising a semiconductor substrate. In addition, the method comprises applying or introducing a precursor substance onto or into the carrier structure. Moreover, the method comprises treating the precursor substance for producing a porous matrix structure. Furthermore, the method comprises introducing a functionalization substance into the porous matrix structure.

The method described offers advantages over conventional methods since the porous matrix structure into which the functionalization substance is introduced is manufactured by treating the precursor substance within or on the semiconductor device. Due to separate manufacturing of the porous matrix structure, in particular, substances which are sensitive to conventional semiconductor production processes may be used as the functionalization substance. Semiconductor production processes such as applying or introducing the precursor substance or treating the precursor substance, for example, may be detrimental to certain functionalization substances since high temperatures or pressures may be employed for said processes, for example. Also, with the method described, a contact between the functionalization substance and etching liquids, which may also be detrimental to the functionalization substance, may be avoided. Therefore, the method is particularly advantageous since a selection of functionalization substances need not be restricted on the grounds of process parameters. In addition, the method described is advantageous in terms of low-cost production of the semiconductor device since all of the method steps may be performed, e.g., on one substrate (e.g. one wafer).

Aluminum, which is deposited with a thickness (0.1 to 10 μm, advantageously 300 nm) which may be employed for the porous matrix layer formation may be used, for example, for the precursor substance mentioned in the method. Applying or introducing the aluminum may be performed, e.g., by means of chemical vapor deposition or cathode sputtering. Once the aluminum has been applied or introduced, further patterning (structuring) may be performed, which involves electrical contacts, conductor lines and an area which is used for subsequent production of the porous matrix structure. The electrical contacts, conductor lines and the area which serves to produce the porous matrix structure are connected to one another in an electrically conducting manner and are also connected to an electrode which is advantageously located at an edge of a carrier (e.g. a wafer). Further steps of the method may include removal of a photoresist layer and cleaning sequences. Once the precursor substance, e.g. aluminum, has been applied or introduced, or has been patterned, a passivation layer, advantageously made of silicon oxide and/or silicon nitride, may be deposited. The passivation layer may be patterned by means of etching processing, for example, in which process electrical terminals, areas which serve to produce the porous matrix structure, and edge contacts are exposed. For treating the precursor substance (e.g., in this case, anodic oxidation), the semiconductor device is introduced into an electrolyte solution, which may include, in order to improve conductivity, substances which are commonly used for said purpose, e.g. sulfuric or oxalic acid, for example. While the semiconductor device is within the electrolyte solution, the precursor substance is modified, by selectively applying a voltage to said precursor substance, e.g. via the edge contacts (e.g. of the wafer), such that the porous matrix structure comes into being, while possible further circuit configurations which may also be located on the semiconductor device undergo no change since no voltage is applied to them. By applying the voltage (5 to 25 volts, wherein a pore size may be adjusted by means of the voltage, advantageously 9 volts), the aluminum is electrochemically modified, resulting in porous aluminum oxide which is subsequently available as a porous matrix structure. Once the porous matrix structure has been produced, the functionalization substance may be absorbed by introducing the semiconductor device into a solution containing the functionalization substance. Subsequently, a compaction step may be performed in order to stabilize the functionalization substance within the porous matrix structure, e.g. by using water or water vapor.

Alternatively, polycrystalline silicon, for example, may serve as the precursor substance. For example, polycrystalline silicon may be applied onto or introduced into the carrier structure by means of chemical vapor deposition, wherein a grain size of the crystallites of the polycrystalline silicon may be adjusted as a function of a deposition temperature used in chemical vapor deposition. In accordance with embodiments, layer thicknesses of 0.1 to 1 µm of polycrystalline silicon are introduced by deposition onto or into the semiconductor device. This layer thickness of the polycrystalline silicon (as the precursor substance) defines a thickness of the porous matrix structure. The resulting porous matrix structure consequently comprises porous silicon which comes into being by treating the polycrystalline silicon. Once the polycrystalline silicon has been deposited, further process steps such as intermediate-oxide deposition, contact-hole etching, metallization, metal patterning, and passivation may be performed. For treating the polycrystalline silicon, the polysilicon layer may be exposed, if need be, by removing the intermediate oxide and the passivation layer. Subsequently, a further protective layer may be applied, for example consisting of a photoresist and covering further structures of the semiconductor device, except for the polysilicon layer to be treated. The semiconductor device may now be dipped into hydrofluoric acid, and a voltage may be applied to a contact conductingly connected to the polysilicon layer. As a result, the polysilicon layer (the precursor substance) presents an anode which is dipped into hydrofluoric acid together with a cathode, advantageously made of platinum. As a result, the polycrystalline silicon is anodically oxidized, and the silicon dioxide which arises in the process is dissolved by the hydrofluoric acid. During the treatment (oxidation and etching), pores are formed within the polysilicon. A pore size of the porous silicon may be influenced by the voltage applied or by the size of the crystallites of the polysilicon. Thereafter, a photoresist may be removed by using a solvent which absorbs no water in order to avoid that the pores of the porous matrix structures are dehydrated and are therefore contaminated by photoresist residues. Then a solvent containing the functionalization substance may be introduced into the pores of the porous matrix structure, e.g. by dipping it into the solvent. For introducing the functionalization substance, the pores may be dried prior to introduction and subsequently may be loaded with a solvent containing the functionalization substance. Thereafter, the solvent may be removed from the pores by means of, e.g., supercritical drying or pentane drying, the functionalization substance remaining within the pores or on the porous matrix structure. Subsequently, sealing of the pores, e.g. by means of a plasma process and/or water vapor, may occur.

In accordance with embodiments of the invention, treating said precursor substance includes electrochemical oxidation and possibly etching of the precursor substance. Treating the precursor substance by means of electrochemical modification enables simple production of the porous matrix structure, e.g. by dipping the semiconductor device, or the precursor substance, into a suitable solution.

In accordance with embodiments, a voltage is applied to the precursor substance during electrochemical modification of the precursor substance. By applying a voltage, a desired pore size of the porous structure may be advantageously adjusted, and, therefore, a quantity of functionalization substance which may be introduced into the porous matrix structure may be advantageously adjusted. The process described here may also be referred to as an electro etching process, wherein the precursor substance serves as an anode and wherein a cathode is dipped, together with said anode, into an electrolyte solution, the desired voltage between the anode and the cathode being adjusted.

In accordance with embodiments, the method comprises application of a passivation layer following application of the precursor substance and prior to treatment of the precursor substance, the precursor substance consequently being partly covered by the applied passivation layer. By means of the passivation layer, structures may be protected during treatment (e.g. during anodic oxidation), so that they will not be modified by the treatment.

In accordance with embodiments, the precursor substance consists of aluminum or polysilicon. Aluminum or polysilicon are advantageous since they may be treated by using simple steps. In particular, e.g., a conducting porous matrix structure may be produced by using polysilicon, or a non-conducting porous matrix structure may be produced by using aluminum (e.g. by means of anodic oxidation).

In accordance with embodiments, the precursor substance is applied onto the semiconductor substrate, an oxide layer of the carrier structure, a nitride layer of the carrier structure or a semiconductor layer of the carrier structure. By applying the precursor substance to an oxide layer or a nitride layer, the precursor substance may readily be electrically insulated from electrically sensitive components. In addition, application of the precursor substance onto the semiconductor substrate offers the possibility of direct electric interaction of the porous matrix structure, which is formed therefrom, with circuit configurations formed within the semiconductor substrate.

In accordance with embodiments of the invention, the functionalization substance is based on a triphenylmethane dye, an azo dye, a stilbene dye, ORMOCER®s, a quaternary ammonium compound, or a metal complex. The functionalization substances mentioned may readily be introduced into the porous matrix structure, for example by means of dip coating, and enable implementation of a sensor component.

Embodiments in accordance with the invention provide a semiconductor device comprising a semiconductor substrate, wherein the semiconductor substrate comprises a plurality of integrated circuit configurations. In addition, the integrated circuit configurations comprise a layer having a porous matrix structure, wherein a functionalization substance is introduced into the porous matrix.

The semiconductor device mentioned is based on the idea that a porous matrix structure which is produced such that it is integrated into a semiconductor device may be advantageously provided with a functionalization substance. What is advantageous here, in particular, is that the porous matrix structure is initially produced without the functionalization substance within the semiconductor device and is subsequently provided with a desired functionalization substance (is filled with same or has same introduced therein in any other manner). In this context, sensitive functionalization substances may be employed for which treatment or shared application with the porous matrix structure may be harmful, in which process the functionalization substances may lose their functions. In addition, the semiconductor device described is advantageous since the porous matrix structure may be produced on a carrier along with the remaining device and may thus be produced at low cost by means of common semiconductor processes.

In accordance with embodiments, the layer comprising the porous matrix structure is integrated into the semiconductor device by means of a chemical bond without any adhesive. The layer described is advantageous since such a porous matrix structure is advantageous for an integrated manufacturing process, i.e. may be formed on a wafer along with other structures, e.g. circuit configurations. In addition, by saving an adhesive layer, cost for the adhesive material, or the adhesion step, may be reduced. Likewise, a negative influence of adhesive layers may be avoided.

In accordance with embodiments, the functionalization substance is a sensor material, said sensor material having a property which depends on a state of a fluid which is in contact with the sensor material. Loading of the porous matrix structure with the sensor material enables production of sensitive components which can react to physical or chemical properties of the fluid.

In accordance with embodiments, the circuit configurations are configured to sense a or the property of the sensor material. Here, the semiconductor device is configured to sense a state of the fluid on the basis of the property of the sensor material. The semiconductor device described may sense the property of the sensor material via the circuit configurations. The property may be influenced, e.g., on the basis of an interaction of the sensor material and the fluid. In addition, a multitude of sensor-system components may be implemented by introducing a sensor material.

In accordance with embodiments of the invention, the sensor material is configured to influence a conductivity of the integrated circuit configurations on the basis of a state of the fluid. Here, the semiconductor device is configured to sense a state of the fluid on the basis of the conductivity influenced. By means of the semiconductor device described, sensitive resistors may be readily implemented, which may be used, e.g., for sensing gas compositions or gaseous states.

In accordance with embodiments, the integrated circuit configurations comprise an optically sensitive area, the porous matrix structure being arranged in a direction of incident light of the optically sensitive area. Here, the sensor material is configured to influence an electric signal of the optically sensitive area on the basis of a state of the fluid, wherein the semiconductor device is further configured to sense a state of the fluid on the basis of the influence exerted on the electric signal. The semiconductor device described may be used, e.g., for implementing sensors within the fluidics (e.g. gas sensors) on the basis of optical signals.

In accordance with embodiments of the invention, the optically sensitive area is configured to receive light through the porous matrix structure, wherein the light undergoes an absorption through the sensor material in the porous matrix structure on the basis of a state of the fluid.

The semiconductor device described may thus detect states of a fluid (e.g. composition or temperature) on the basis of simple differences in brightness.

In accordance with embodiments, the optically sensitive area is adapted to receive light generated by luminescence within the porous matrix structure on the basis of an interaction of the fluid and the sensor material. By means of the embodiment described, e.g., an external illumination source may be dispensed with since the optical signals are based on luminescence which is detectable without any external illumination.

In accordance with embodiments of the invention, the optically sensitive area is designed to receive light, the light undergoing a refraction within the porous structure on the basis of a state of the fluid. In addition, the semiconductor device is designed to sense, on the basis of the refraction, the state or a state of the fluid. The semiconductor device described may sense, e.g., the deflection of a light beam and may readily recognize, on the basis thereof, whether or not, e.g., a change in a state (e.g. composition or optical polarization) of the fluid has occurred.

In accordance with embodiments, the sensor material is designed to influence, on the basis of a state of the fluid, a capacitive and/or resistive portion of a capacitance of the integrated circuit configurations, the semiconductor device being configured to sense a state (e.g. composition or temperature) of the fluid on the basis of the capacitance which has been influenced. The semiconductor device described enables simple implementation of, e.g., capacitors suitable for sensor technology in fluidic applications.

In accordance with embodiments, the sensor material is designed to influence, on the basis of a state of the fluid, a work function of a semiconductor portal of the integrated circuit configurations. In addition, the semiconductor device is configured to sense a state of the fluid on the basis of the work function which has been influenced. The semiconductor device described may be employed, e.g., for generating sensitive transistors, e.g. suspended (or floating) gate transistors.

In accordance with embodiments, the porous matrix structure is based on an electrically conducting material. By using a precursor substance of polysilicon, e.g., an electrically conducting porous matrix structure may be readily generated by means of anodic oxidation of the polysilicon. The porous matrix structure resulting therefrom may consist of porous silicon and may therefore be conducting. By introducing, e.g., a functionalization substance configured to modify a conductivity of the porous matrix structure on the basis of a state of the fluid, sensitive resistors may thus be readily implemented.

In accordance with embodiments, the porous matrix structure is based on an electrically insulating material. For this purpose, e.g. aluminum or polysilicon may be used as the precursor substance for the porous matrix structure; either aluminum oxide or quartz may arise due to oxidation. The porous matrix structure may thus consist of, e.g., porous aluminum oxide or porous quartz. The porous matrix structure described is particularly suited, e.g., as a dielectric for capacitors.

In accordance with embodiments, the porous matrix structure is optically transparent. An optically transparent matrix structure may be advantageously employed for implementing, e.g., optically sensitive components based on the transmission of light.

In accordance with embodiments, the porous matrix structure is based on a precursor substance. In addition, a thickness of the porous matrix structure is based on a thickness of the precursor substance. The thickness, which may thus be adjusted, of the porous matrix structure may be advantageously employed so as to be able to absorb (or store) a specific (defined) quantity of the functionalization substance.

In accordance with embodiments, the functionalization substance is based on a triphenylmethane dye, an azo dye, a stilbene dye, ORMOCER®s, a quaternary ammonium compound, or a metal complex. Functionalized semiconductor devices may readily be generated by means of the functionalization substances mentioned (e.g. for sensor-technology applications).

In accordance with embodiments, the porous matrix structure is applied onto the semiconductor substrate, an oxide layer of the carrier structure, a nitride layer of the carrier structure, or a semiconductor layer of the carrier structure. By applying the porous matrix structure onto an oxide layer or a nitride layer of the carrier structure, an insulated porous matrix structure, e.g., may be generated which is not directly connected, e.g., to the circuit configurations of the semiconductor device. By applying the porous matrix structure onto the semiconductor substrate or a semiconductor layer of the carrier structure, electric coupling of the porous matrix structure with the semiconductor device may be effected (e.g. via the circuit configurations) in a simplified manner, for example.

In accordance with embodiments, the porous matrix structure consists of aluminum oxide, quartz, or porous silicon. A porous matrix structure consisting of aluminum oxide or quartz may advantageously be employed as an electrically insulating porous matrix structure. In addition, a porous matrix structure made of porous silicon may advantageously serve as an electrically conductive porous matrix structure.

In accordance with embodiments, the functionalization substance is configured to perform a bonding with a further porous matrix structure, the further porous matrix structure being loaded with the functionalization substance. The device described may be advantageously used for connecting several semiconductor devices (e.g. in a interconnection technology or in subsequent manufacturing of relatively large arrangements comprising several porous matrix structures or circuit configurations).

BRIEF DESCRIPTION OF THE DRAWINGS

Embodiments of the present invention will be detailed subsequently referring to the appended drawings, in which:

FIGS. 2a-e show a method of producing a photodiode in accordance with embodiments of the present invention;

FIGS. 3a-d show a method of producing a transistor in accordance with embodiments of the present invention;

FIGS. 4a-c show a method of producing a resistor in accordance with embodiments of the present invention;

FIGS. 7a-b show a capacitor in accordance with embodiments of the present invention.

DETAILED DESCRIPTION OF THE INVENTION

Figure 1:
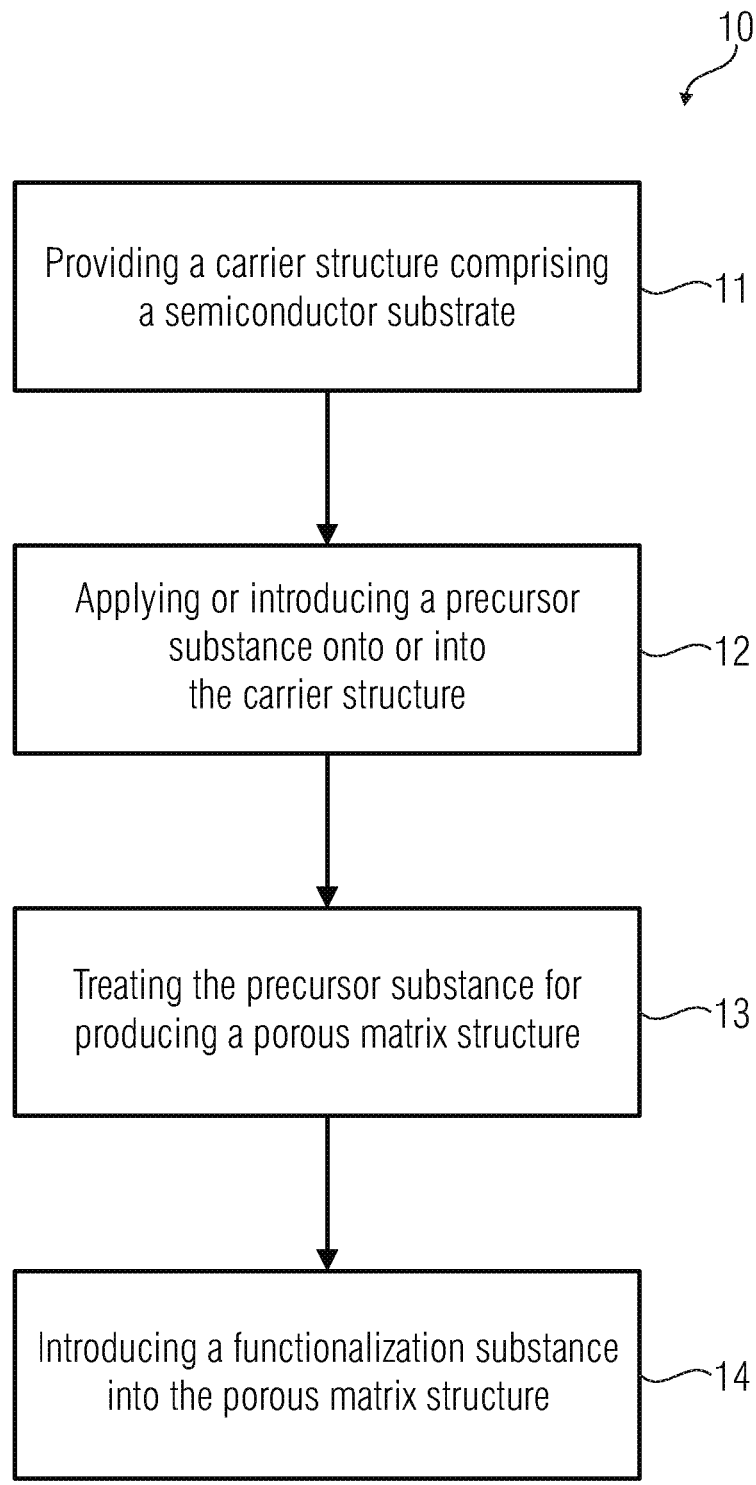
FIG. 1 shows a method in accordance with embodiments of the present invention.

FIG. 1 shows a method 10 in accordance with embodiments of the present invention. The method 10 includes a step of providing 11 a carrier structure comprising a semiconductor substrate. The carrier structure may be a silicon wafer, for example. A precursor substance is applied onto or introduced into the carrier structure 12. Precursor substances may be polysilicon or aluminum, for example. In addition, the precursor substance is treated 13, so that a porous matrix structure will be generated. The treatment may comprise anodic oxidation, for example. The method 10 further comprises introducing 14 of a functionalization substance into the porous matrix structure.

The method 10 described is particularly advantageous since the porous matrix structure is produced in a separate step, i.e. the functionalization substance may be introduced following the step of treating the precursor substance. In other words, the porous matrix structure is generated by treating the precursor substance while the functionalization substance need not undergo said treatment. This is of great advantage in particular with regard to sensitive functionalization substances since the functionalization substances might lose their functions as a result of the above-mentioned treatment of the precursor substance. Since treatment may also include warming or etching, for example, this is disadvantageous for a large selection of potential functionalization substances since they might be damaged in the process, as was already mentioned. In addition, functionalization substances may thus be introduced which exhibit long-term stability, for example, i.e. only exhibit a small amount of aging phenomena. In addition, the method is advantageous in terms of manufacturing since generating of the porous matrix structure by treating 13 the precursor substance may be performed in a manufacturing process that is typical of semiconductor technology. In other words, the entire method 10 may be performed on a wafer, for example, without having to apply separately patterned elements onto the wafer. Moreover, following manufacturing of the device on, e.g., a wafer, the method may comprise sawing of the wafer so as to remove the generated device from the wafer.

FIGS. 2a to d show an embodiment of a method of producing a photodiode, the method comprising further optional steps in addition to the steps mentioned with reference to the method 10.

Figure 2A:
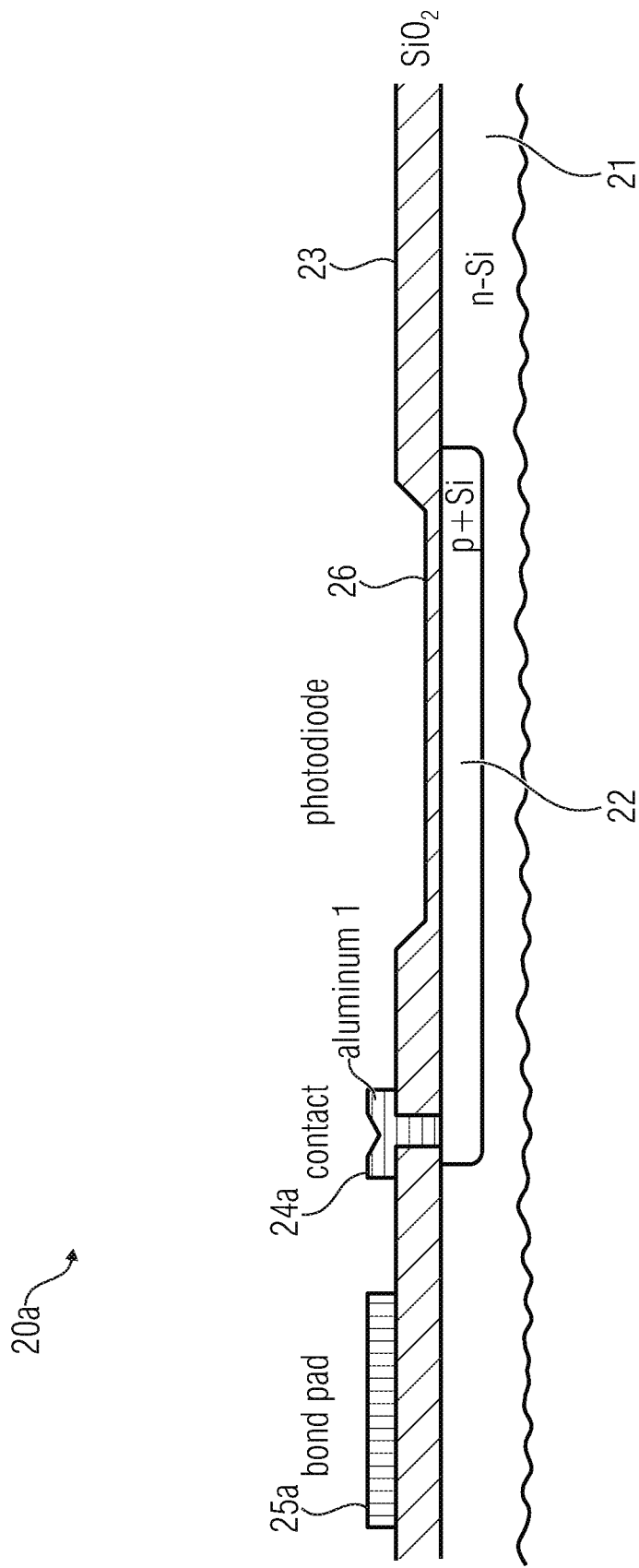

FIG. 2a shows a photodiode 20a manufactured on a semiconductor substrate 21 made of negatively doped silicon. The semiconductor substrate 21 serves both as a cathode of the photodiode 20a and as a carrier structure of the photodiode 20a. The surface of the semiconductor substrate 21 has an area with positively doped silicon 22 implemented therein, which serves as an anode of the photodiode 20a. In addition, the photodiode 20a comprises an insulating layer 23 made of silicon dioxide, which is implemented across the cathode 21 and the anode 22 of the photodiode 20a in a planar manner. A contact 24a to the anode 22 of the photodiode 20a is implemented through the insulating layer 23. The contact 24a is connected to a contacting point 25a, also referred to as a bond pad, in an electrically conducting manner. Moreover, the photodiode 20a comprises a depression 26 of the insulating layer 23 across an area of the anode 22 of the photodiode 20. The depression 26 results in that light can better impinge upon the anode 22 through the insulating layer 23 since in the area of the depression 26, the insulating layer 23 is configured to be thinner than in the rest of the insulating layer 23. In the following, the photodiode 20a will be used as a carrier structure for a method in accordance with the invention. FIG. 2b shows the photodiode 20b of FIG. 2a following application or introduction of a precursor substance onto/ into the carrier structure, in this case the photodiode 20a. With the precursor substance shown here, the metal at hand is aluminum, and the application results in that the contact point 25a and the contact 24a undergo broadening, so that a contact point 25b and a contact 24b result therefrom. In addition, the depression 26 has an aluminum layer 26a deposited therein which serves as a precursor for the porous matrix structure. In addition, the aluminum layer 26a is connected to a conductor line 27 in an electrically conducting manner. FIG. 2c shows an optional step following deposition of the precursor substance. To this end, a passivation layer 28 is applied across the structure of FIG. 2b, i.e. photodiode 20b. The passivation layer 28 is subsequently opened within the area of the contact point 25b as well as in the area of the aluminum layer 26a, in which process the photodiode 20c is shaped. A left-hand portion 26a' of the aluminum layer 26a and a right-hand portion 26a" of the aluminum layer 26a is covered by the passivation 28. The passivation 28 may serve, e.g., to avoid short-circuits with adjacently arranged conducting objects. FIG. 2d shows a photodiode 20*d*, wherein the precursor substance 26*a*, e.g. aluminum, has been transformed to a porous matrix structure 26*b* by means of etching, the right-hand portion 26*a*″ and the left-hand portion 26*a*′ remaining as elementary aluminum. To this end, a voltage was applied to the conductor line 27, whereas the photodiode 20*d* was dipped into an electrolyte solution during an anodic oxidization process (the conductor line 27 advantageously leads to an edge of the component, e.g. a wafer edge, where said conductor line may be contacted during dipping). Since during anodic oxidation, the contact point 25*b* is not at the same potential as the aluminum layer 26*a*, it will be exempt from treatment. This means that the contact point 25*b* keeps its electric and chemical properties, whereas the aluminum layer 26*a* is oxidized to form aluminum oxide 26*b*. The right-hand portion of the aluminum 26*a*″ and the left-hand portion 26*a*′ of the aluminum maintain their respective shape and are not oxidized since they are covered by the passivation layer 28. The aluminum oxide layer 26*b* is not electrically conducting and may subsequently be loaded with a functionalization substance. This may readily occur in that the photodiode 20*d* is dipped into a solution containing the desired functionalization substance. To improve contacting during etching, the conductor line 27 is guided, outside the drawing plane, in such a manner that contacting of the photodiode 20*d* is possible at an edge, so that as much of the entire photodiode as possible may be dipped into the etching solution. FIG. 2*e* shows the photodiode 20*d* in a top view. The conductor line 27 here is depicted as a conductor line leading to a wafer edge and connecting further matrix elements so as to be able to apply the voltage for anodic oxidation. The porous matrix structure 26*b* may be seen as a rectangular face in the top view of FIG. 2*e*. The rectangular face of the porous matrix structure 26*b* is bordered by the passivation 28, which still has some of the untreated aluminum located underneath it (left-hand portion 26*a*′ and right-hand portion 26*a*″). Moreover, the contact point 25*b* may be recognized as a rectangular face bordered by the passivation 28. The contact point 25*b* is connected to the contact 24*b* via the conductor line 25*b*′. As a result, contacting of the anode 22 of the photodiode 20*d* continuous to be possible. In addition, FIGS. 2*a-e* describe integration of an aluminum-based matrix layer by using the example of a photodiode.

General aspects of photodiodes in accordance with embodiments of the invention will be addressed below. In accordance with embodiments, a light entrance face 26 of a photodiode has a porous matrix structure and the reactive coating applied thereto (e.g. into the porous matrix structure). The reactive coating reacts to analytes (e.g. fluids) or to a change in physical parameters by changing optical properties, which are then forwarded as electrical signals. Changes in optical properties may be, for example: a change in an absorption spectrum, a change in a polarization, a change in an emission spectrum and/or a change in a refractive index.

Figure 3A:
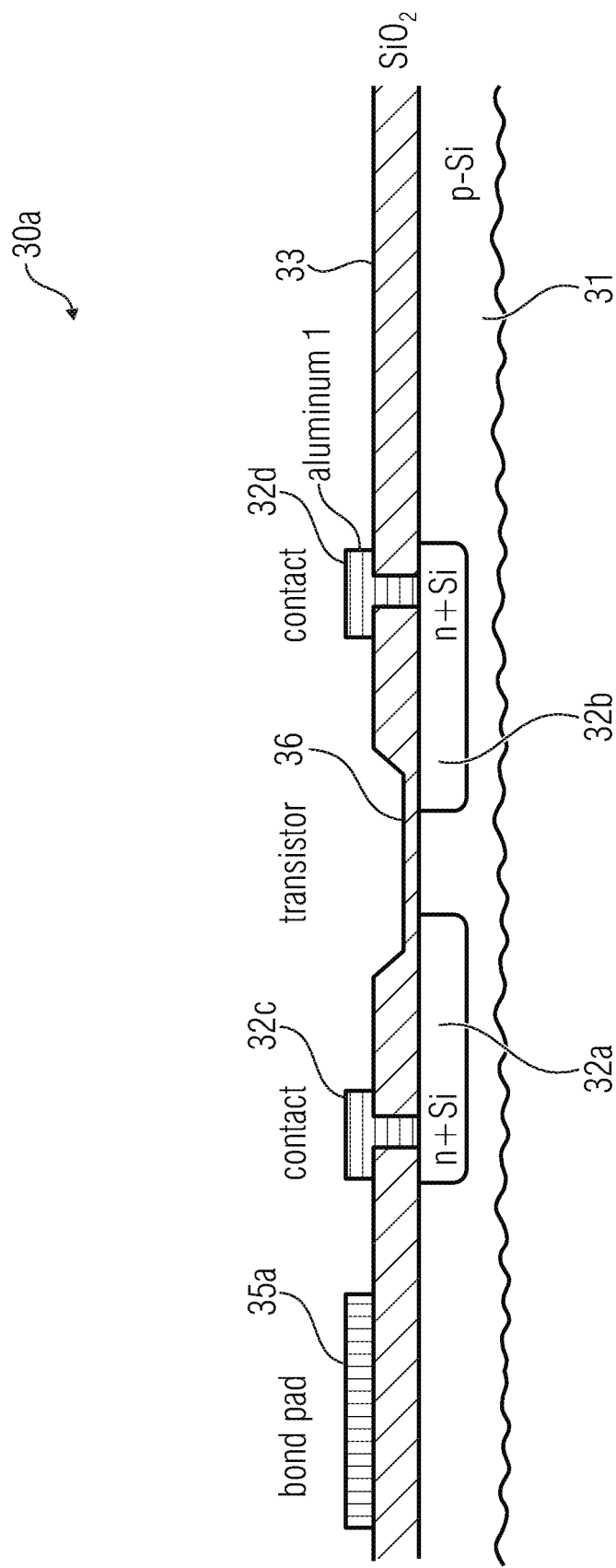
Figure 3C:
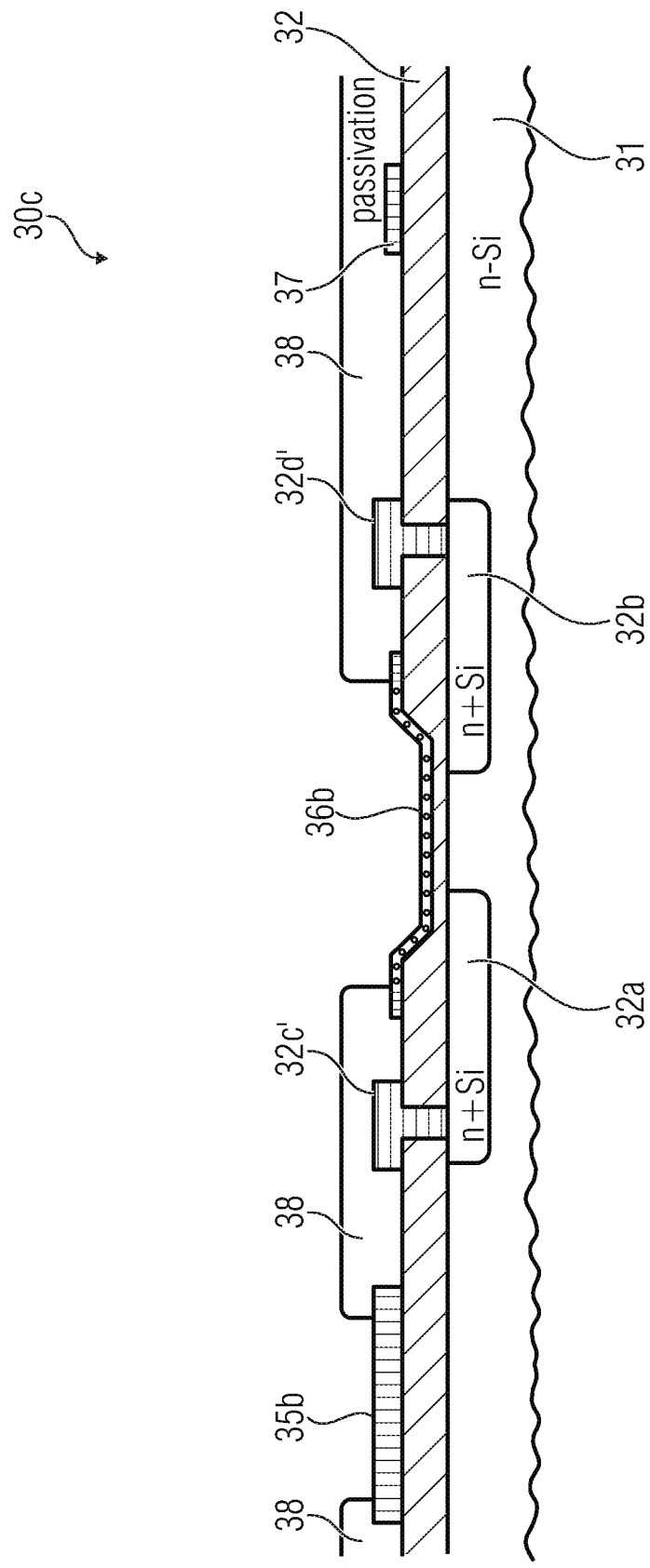
Figure 3D:
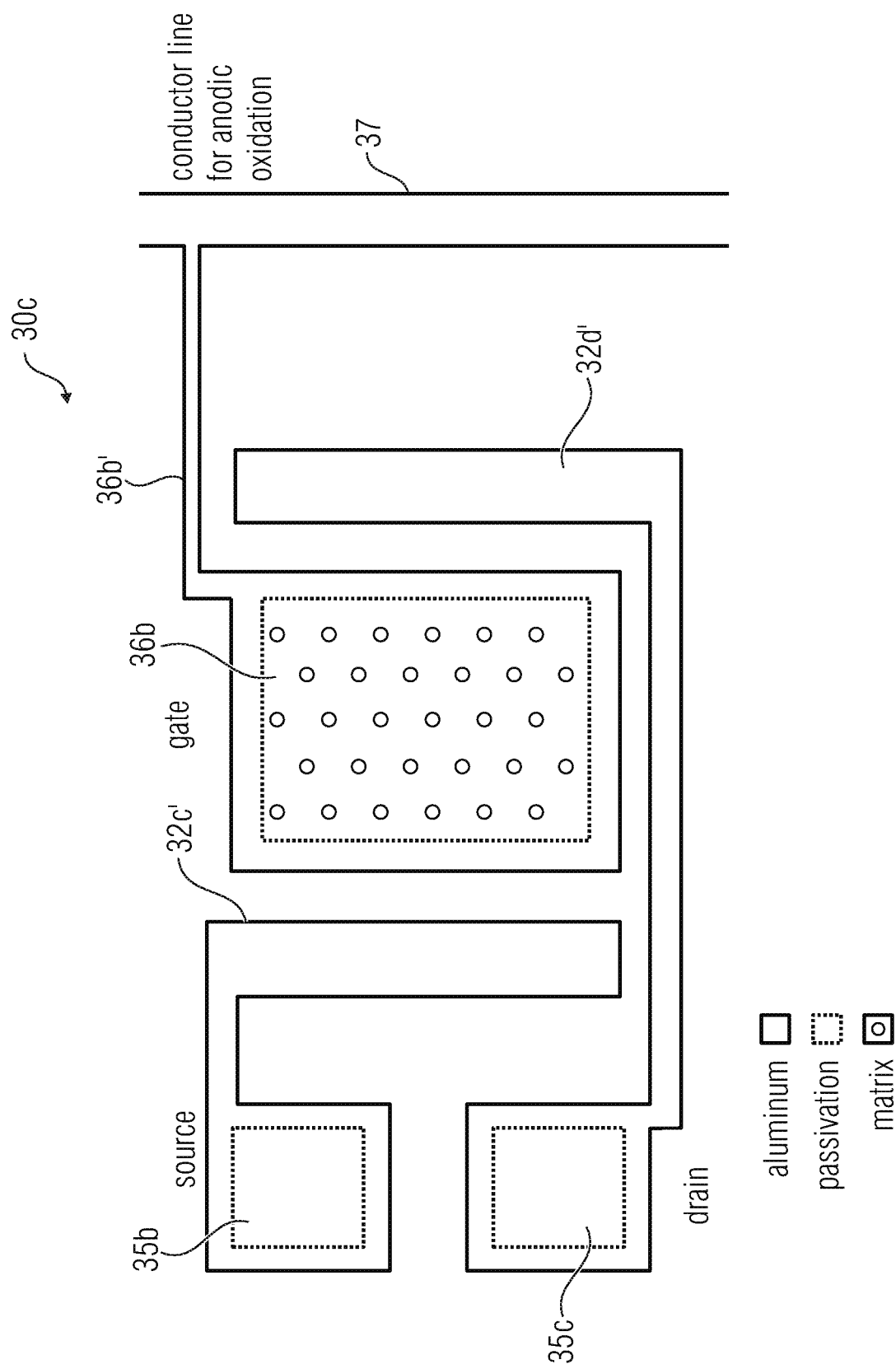

FIGS. 3*a* to *c* show a method as well as a transistor in accordance with embodiments of the present invention. FIG. 3*a* depicts a carrier structure 30*a* which is similar to a field effect transistor in terms of its main features. The carrier structure 30*a* serves to manufacture a transistor in accordance with the invention. Here, a method in accordance with embodiments of the invention is applied. The carrier structure 30*a* is implemented on a positively doped silicon substrate 31 in that a source electrode 32*a* is implemented with negatively doped silicon, and a drain electrode 32*b* is implemented with negatively doped silicon. The substrate 31, the source electrode 32*a* and the drain electrode 32*b* are fabricated within one layer. An insulating layer 33 made of silicon dioxide and comprising a depression 36 in the area above and between the source electrode 32*a* and the drain electrode 32*b* extends across the layer. In addition, a contact 32*c* to the source electrode 32*a* and a contact 32*d* to the drain electrode 32*b* are guided through the insulating layer 33. In addition, the carrier structure 30*a* comprises a contacting point 35*a* which may be connected either to the contact 32*c* or to the contact 32*d* in a conducting manner. FIG. 3*b* shows an intermediate step of the method, which produces a structure 30*b*. In comparison to structure 30*a*, structure 30*b* comprises an unchanged semiconductor layer comprising the substrate 31, the source electrode 32*a* and the drain electrode 32*b*. The layer continues to have the insulating layer 33 located thereon, onto which a new aluminum layer has been deposited which was subsequently patterned. By means of the patterning, the contact point 35*a*, the contacts 32*c* and 32*d* were expanded, so that a contact point 35*b* as well as contact 32*c*′ and contact 32*d*′ have come into being. In addition, the structure 30*b* comprises an aluminum layer 36*a* which has settled in the depression 36 between the source electrode 32*a* and the drain electrode 32*b*. In addition, during application of the precursor substance, in this case aluminum, a conductor line 37 has been produced which is electrically conducting with the aluminum layer 36*a*. Moreover, the conductor line 37 advantageously leads to an edge of the structure 30*b* for improved contacting during anodic oxidation. FIG. 3*c* shows a structure 30*c*, which is modified in relation to structure 30*b* such that a passivation layer 38 has been applied onto areas of the structure 30*b* which are to be protected. The contact point 35*b* as well as the porous matrix structure 36*b*, which has been generated by anodic oxidation of the aluminum layer 36*a*, are exposed. By analogy with FIG. 2*d*, portions to the right and to the left of the aluminum layer are untreated since they were covered by the passivation layer 38 during treatment. To perform the etching, the structure was dipped into an electrolyte solution, and a voltage was applied to the aluminum layer 36*a* via the conductor line 37. In a further step, which is not shown, any functionalization substance may now be introduced into the porous matrix structure 36*b*. Said introduction may be performed, e.g., by simply dipping the structure 30*c* into a solution comprising a functionalization substance. FIG. 3*d* shows a transistor 30*c* in accordance with FIG. 3*c* in a top view. The source contact 32*c*′ is connected to the contact point 35*b* via a conductor line. Moreover, the drain contact 32*d*′ in connected in a conducting manner to a contact point 35*c* via a conductor line. By analogy with the contact point 35*b*, the contact point 35*c* is exposed, so that the contact point 35*c* enables contacting of the drain electrode 32*b*. In addition, the porous matrix structure 36*b* can be recognized as a rectangular face acting as a gate electrode for the transistor 30*c*. Likewise, one can recognize a conductor line 36*b*′, which establishes a connection to the conductor line 37, it being possible to use the conductor line 37 for anodic oxidation. Also, FIGS. 3*a-d* describe integration of an aluminum-based matrix layer by using the example of an aluminum gate transistor.

Figure 4A:
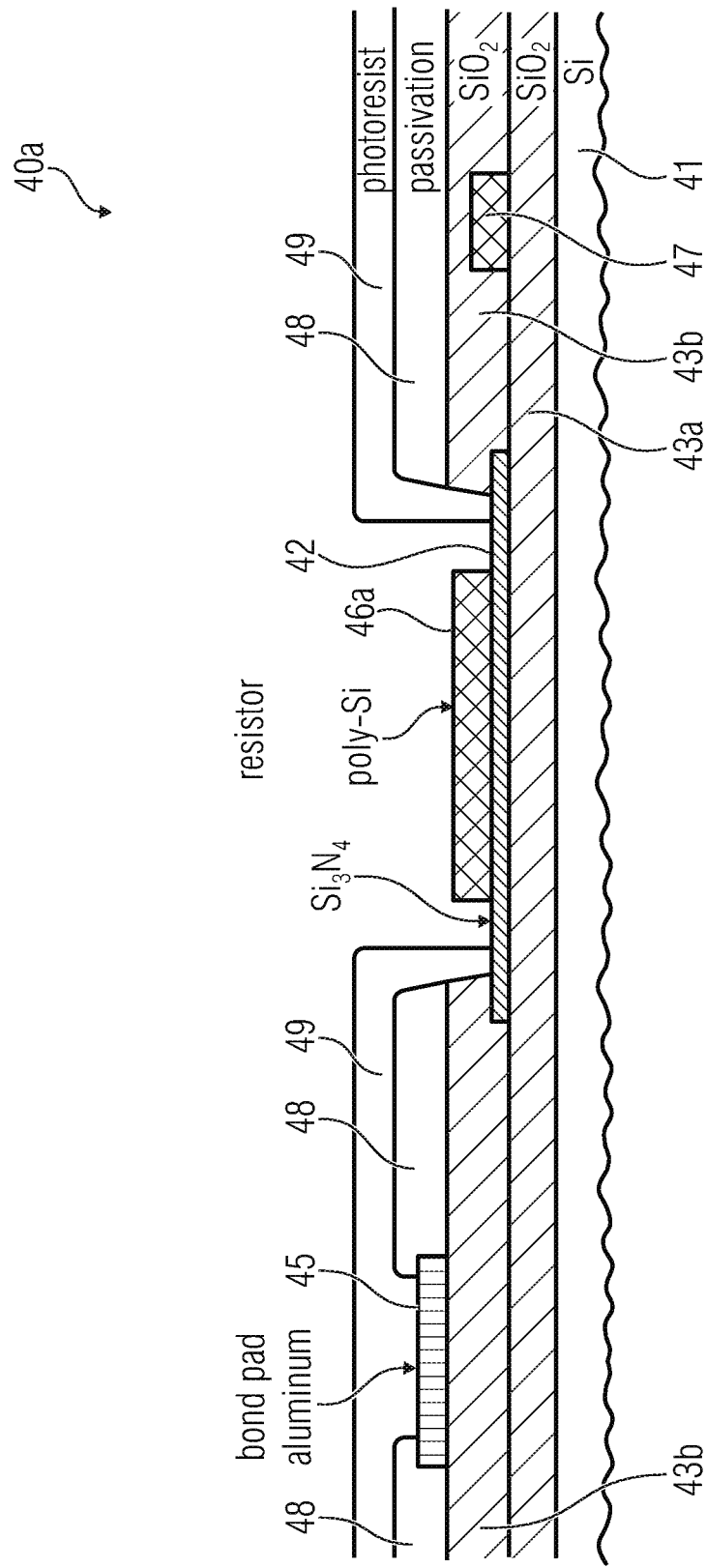
Figure 4C:
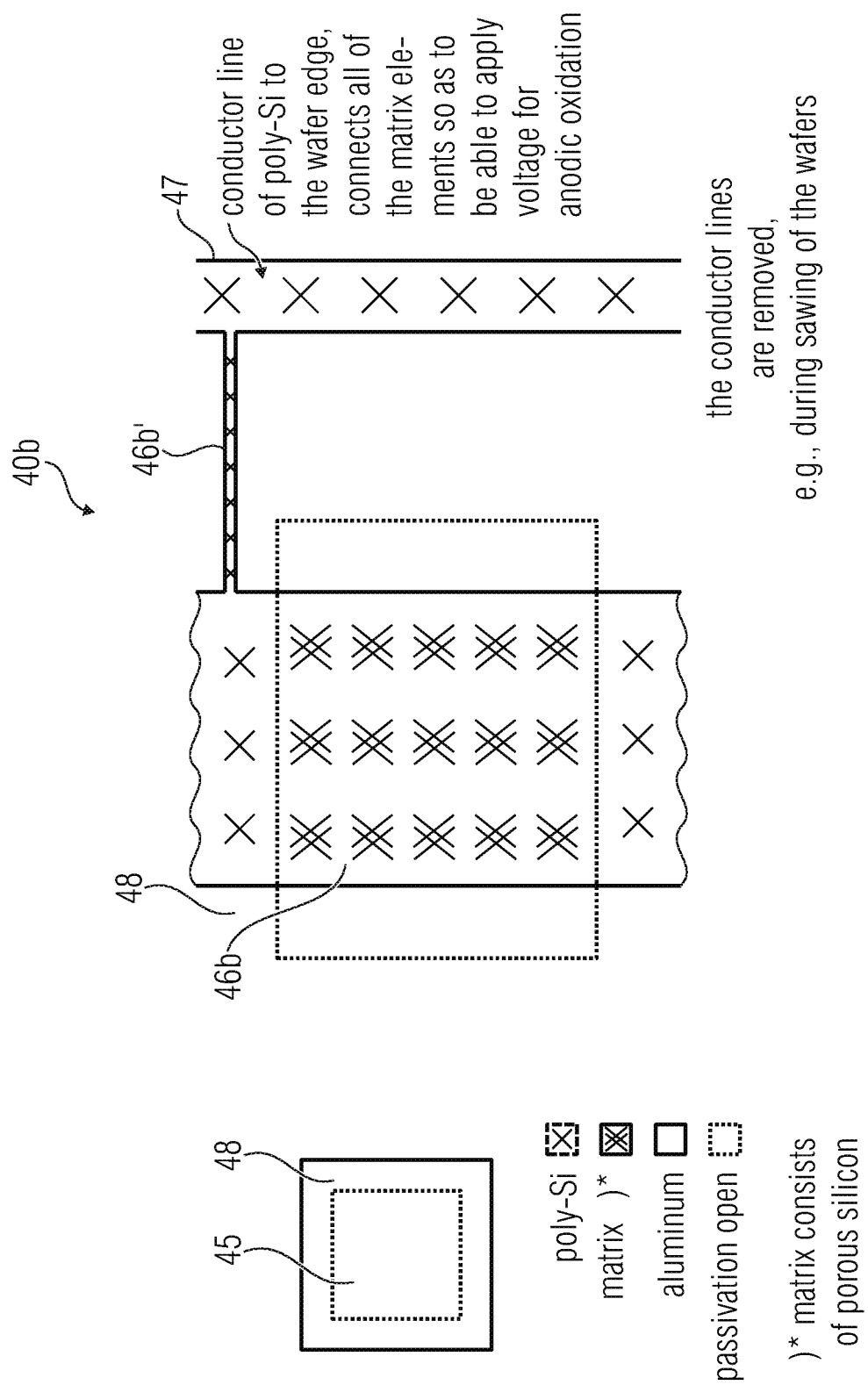

FIGS. 4*a* and *b* show steps of a method in accordance with embodiments of the present invention. The method shown in FIGS. 4*a* and 4*b* is used for obtaining a resistor having a porous matrix structure. To this end, the structure 40*a* is used as a starting point, and said structure comprises a semiconductor substrate 41, e.g. a silicon wafer, and may be implemented within same. The silicon layer 41 has a silicon oxide layer 43*a* deposited thereon as an insulting layer, which in turn has a nitride layer 42, e.g. silicon nitride, centrally applied to it. Additionally, the insulating layer 43a has a further insulating layer 43b applied to it to the right and to the left of the nitride layer 42, said insulating layer 43b having a conductor line 47 made of polysilicon implemented therein. The nitride layer 42 has a polysilicon layer 46a applied thereto which serves as a precursor substance. The polysilicon layer 46a is connected to the conductor line 47 in an electrically conducting manner. The insulating layer 43b has a passivation 48 applied to it as well as a contact point 45 which is not covered by the passivation 48, or has been freed from the passivation 48. The structure 40a is covered by a photoresistive material 49, so that both the contact point 45 and the passivation 48 are covered by same in a planar manner, the polysilicon layer 46a not being covered by it. As a result, the precursor substance is easily accessible to anodic oxidation of the precursor substance so as to obtain a porous matrix structure. FIG. 4b shows the structure 40b following anodic oxidation of the polysilicon layer 46a, in which process a porous silicon layer 46b has been created. In addition, the photoresistive material 49 has been removed. The porous matrix structure 46b may be loaded, in a step which is not shown, with any functionalization substance, or a functionalization substance may be introduced into the porous matrix structure 46b and may be contacted via the contact point 45. On the basis of a state of a gas or a fluid which is in contact with the porous matrix structure 46b, a resistance may now be determined via the contact point 45. As a function of a specific resistance, a statement may consequently be made regarding the gas. FIG. 4c shows the porous resistor 40b in a top view. Here, the porous silicon structure 46b functioning as a porous matrix structure can be seen to be framed by the passivation 48. Moreover, the contact point 45 is exposed and is bordered by the passivation material 48. The polysilicon, or the precursor substance, may be contacted via the conductor line 46b' and 47 during an anodic oxidation process. The conductor line 47 advantageously leads to a wafer edge and connects potential further matrix elements (faces consisting of precursor substance) which are present on a wafer in order to pattern same and/or supply them with a voltage for anodic oxidation. In a further step, the conductor lines, e.g. the conductor line 47, may be removed during sawing of the wafers. By analogy, the conductor lines 27 and 37 may also be removed during sawing of wafers which have the respective structures implemented thereon. Moreover, FIGS. 4a to b show integration of a poly-Si-based matrix layer by using the example of a resistor.

Aspects of resistors in accordance with embodiments of the invention will be generally discussed below. In accordance with embodiments, there are two possibilities for influencing a resistor: a porous conductive layer (e.g. porous silicon) or a porous insulating layer (e.g. aluminum oxide). The manufacturing methods which have already been described in connection with other embodiments may be used for this purpose. A reactive coating may now be changed by an analyte (e.g. gas or fluid) even in terms of its conductivity, or it changes a conductivity of the porous matrix. As was already described, suitable matrix precursor layers (precursor substances) may be introduced during the process and may be transformed into matrix layers and be activated during the further course of the process.

Figure 5:
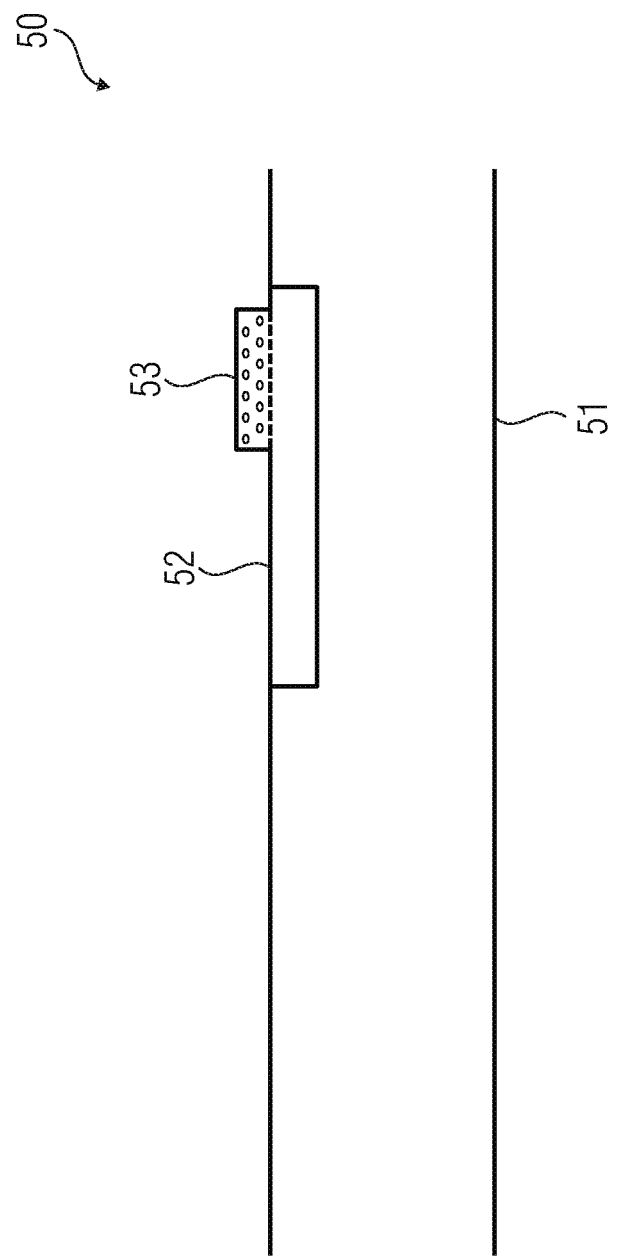
FIG. 5 shows a semiconductor device in accordance with embodiments of the present invention.

FIG. 5 shows a semiconductor device 50 in accordance with embodiments of the present invention. The semiconductor device 50 comprises a semiconductor substrate 51 comprising a plurality of integrated circuit configurations 52. In addition, the integrated circuit configurations 52 comprise a layer 53 having a porous matrix structure. The porous matrix structure 53 has a functionalization substance introduced therein.

The semiconductor device 50 described may be advantageously used for producing sensor-technology components, for example. In particular, a functionalization substance which is sensitive to gas compositions or gas states may be employed so as to sense any of the described states on the basis of a reaction of the functionalization substance via the circuit configurations 52. Moreover, it is advantageous that the porous matrix structure 53 may be introduced into the semiconductor device irrespectively of the functionalization substances. This is advantageous, in particular, since functionalization substances are often sensitive to process steps of semiconductor production technology, in particular, e.g., of the manufacturing of the porous matrix structure. In other words, the functionalization substances or a functionalization substance may be introduced into the porous matrix structure once the porous matrix structure has been produced. In particular, shared application of the functionalization substance and the carrier structure (porous matrix structure) may be dispensed with here since also the process step of applying a precursor substance of the porous matrix structure may harm a functionalization substance.

Figure 6A:
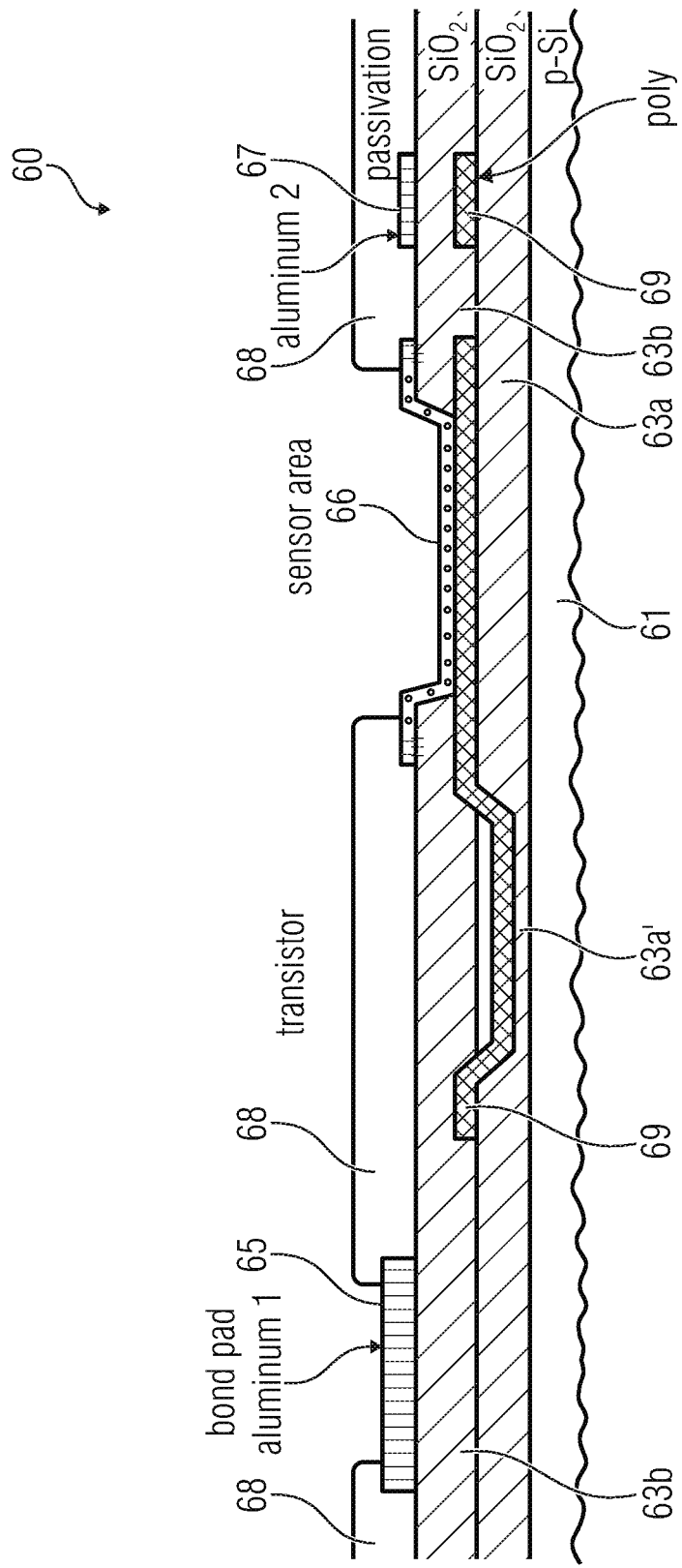
FIGS. 6a-b show a transistor in accordance with embodiments of the present invention.
Figure 6B:
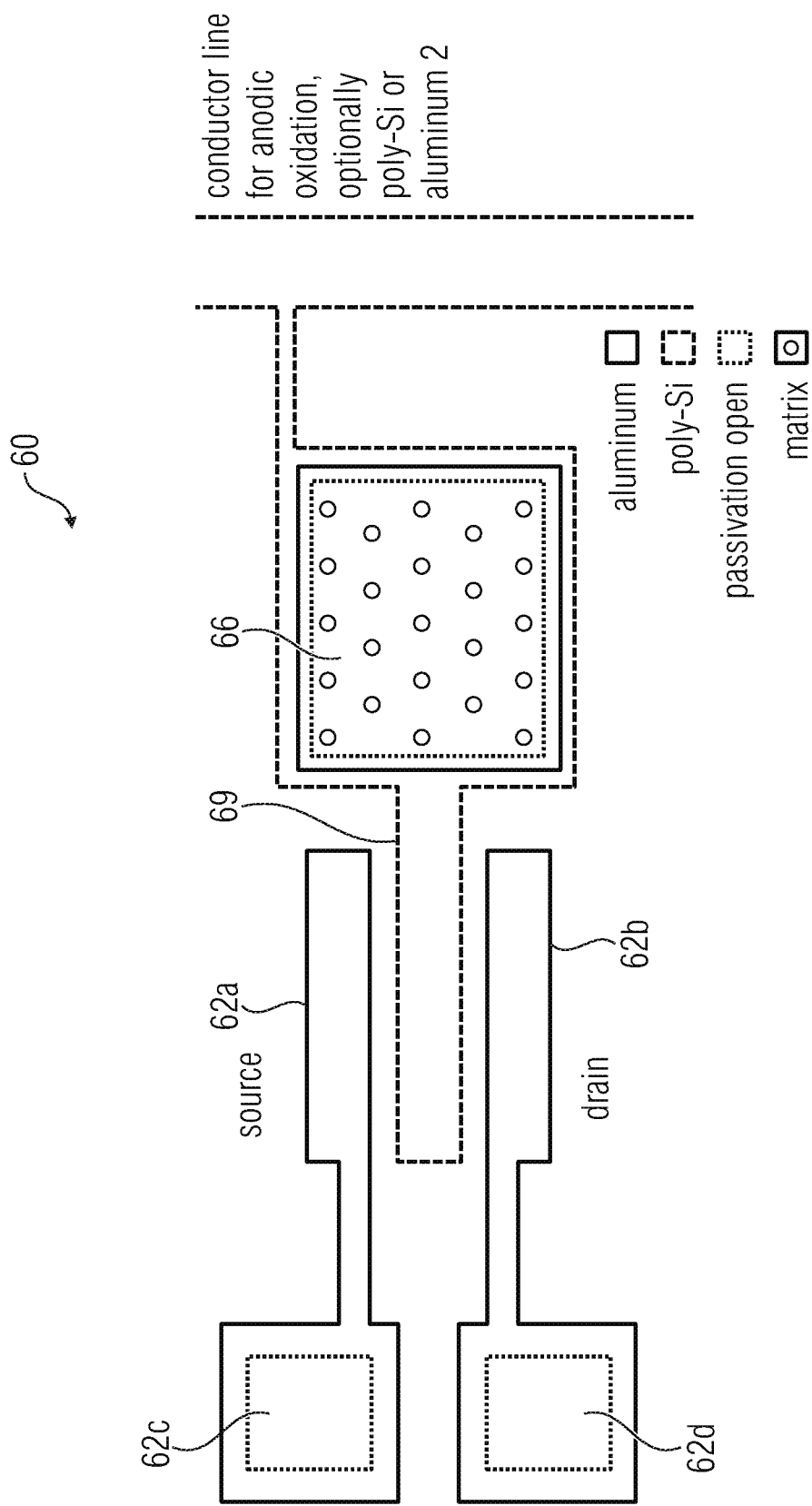

FIG. 6a shows a semiconductor device 60 in accordance with embodiments of the present invention in a cross-sectional view. The semiconductor device 60 implements a transistor comprising a suspended gate, i.e. a transistor whose gate electrode need not be wired to further circuit parts. In other words, a potential of the gate electrode is in a state which is not determined by other circuit parts. The transistor 60 is implemented on a semiconductor substrate 61, here positively doped silicon. Since FIG. 6 shows the gate electrode 69 only, the negatively doped areas of the substrate 61, which act as the source and the drain electrodes, are not visible since they lie outside the drawing plane. The substrate 61 has a first insulating layer 63a made of silicon oxide configured thereon. An area 63a' of the insulating layer 63a is configured to be thinner than the remaining insulating layer 63a, so that a gate electrode 69 arranged on the area 63a' configured to be thinner may better interact electronically with the substrate 61. In other words, in simplified terms, a channel of the transistor may more readily form in the area located below the thinned area 63a'. The first insulating layer 63a has a second insulating layer 63b configured thereon which is made of silicon dioxide. Said second insulating layer 63b forms, together with the gate electrode 69 made of polysilicon, a layer resting on the first insulating layer 63a. The gate electrode 69 has a porous matrix structure 66 arranged thereon which advantageously consists of aluminum dioxide or quartz. Moreover, the second insulating layer 63b has a contact point 65 formed thereon. The contact point 65 may serve to contact, e.g., a source or drain electrode. The structure described is covered by a passivation layer 68, the contact point 65 and the porous matrix structure 66 being exposed. The porous matrix structure 66 may be loaded with a functionalization substance, or a functionalization substance may be introduced into the porous matrix structure 66. On the basis of the functionalization substance and on a fluid or gas reacting with the functionalization substance, a charge may arise within the porous matrix structure 66. On the basis of the charge, the gate electrode 69 may undergo a charge change. On the basis of the charge change of the gate electrode, an electrically conducting channel may form, within an area located below the gate electrode 69, between a source and a drain electrode. FIG. 6b shows the transistor 60 in a top view, wherein the source electrode 62a and the drain electrode 62b are visible in addition to the structures described in FIG. 6a. The source electrode 62a may be contacted via the contact 62c, and the drain electrode 62b may be contacted via the contact 62d. The contacts 62c and 62d may be, e.g., contact 65 in FIG. 6a. The source electrode 62a and the drain electrode 62b have the gate electrode 69 arranged therebetween, which may, given an appropriate charge, connect a conducting channel between the source electrode 62a and the drain electrode 62b. In summary, a charge may be induced on the gate electrode 69 via a functionalization substance introduced into the porous matrix structure 66 and on the basis of a reaction of the functionalization substance. On the basis of the charge induced on the gate electrode 69, the transistor 60 may enable a variable current flow. On the basis of the variable current flow, a state, or a composition, of a fluid which is in contact with the porous matrix structure 66 may be detected. In addition, FIGS. 6a to b show integration of an aluminum-based matrix layer by using the example of a poly-gate transistor.

General aspects of transistors in accordance with embodiments of the invention will be addressed below. In accordance with embodiments, aluminum, which may transformed into a porous aluminum oxide layer by means of known processes, is applied onto a suspended gate made of polysilicon, for example. Instead of the aluminum oxide layer, one may also use porous silicon, which is transformed to porous quartz by means of oxidation. Said non-conducting matrix serves to receive a reactive coating (e.g. functionalization substance). A precondition for a sensor function is that said coating exhibits changes in its properties upon contact with analytes (e.g. gases or, generally, fluids) or upon a change in physical parameters. Such changes may occur, e.g., at the electronic level and be caused, e.g. by a change in electric properties such as work function (Kelvin potential), capacitance, resistance, polarity, or optical properties such as a change in an absorption spectrum, change in an emission spectrum, for example. By applying the starting layers of the matrix (precursor substances) in a targeted manner, matrix layers may be adjusted in a targeted manner which receive a precisely defined amount of the reactive coating. As a result, e.g. sensitivity, selectivity or response time may be varied. Since a matrix thickness determines a received amount of reactive substance (functionalization substance), very simple coating methods are possible, e.g. dip coating (coating by dipping into a solution containing the desired functionalization substance).

Figure 7A:
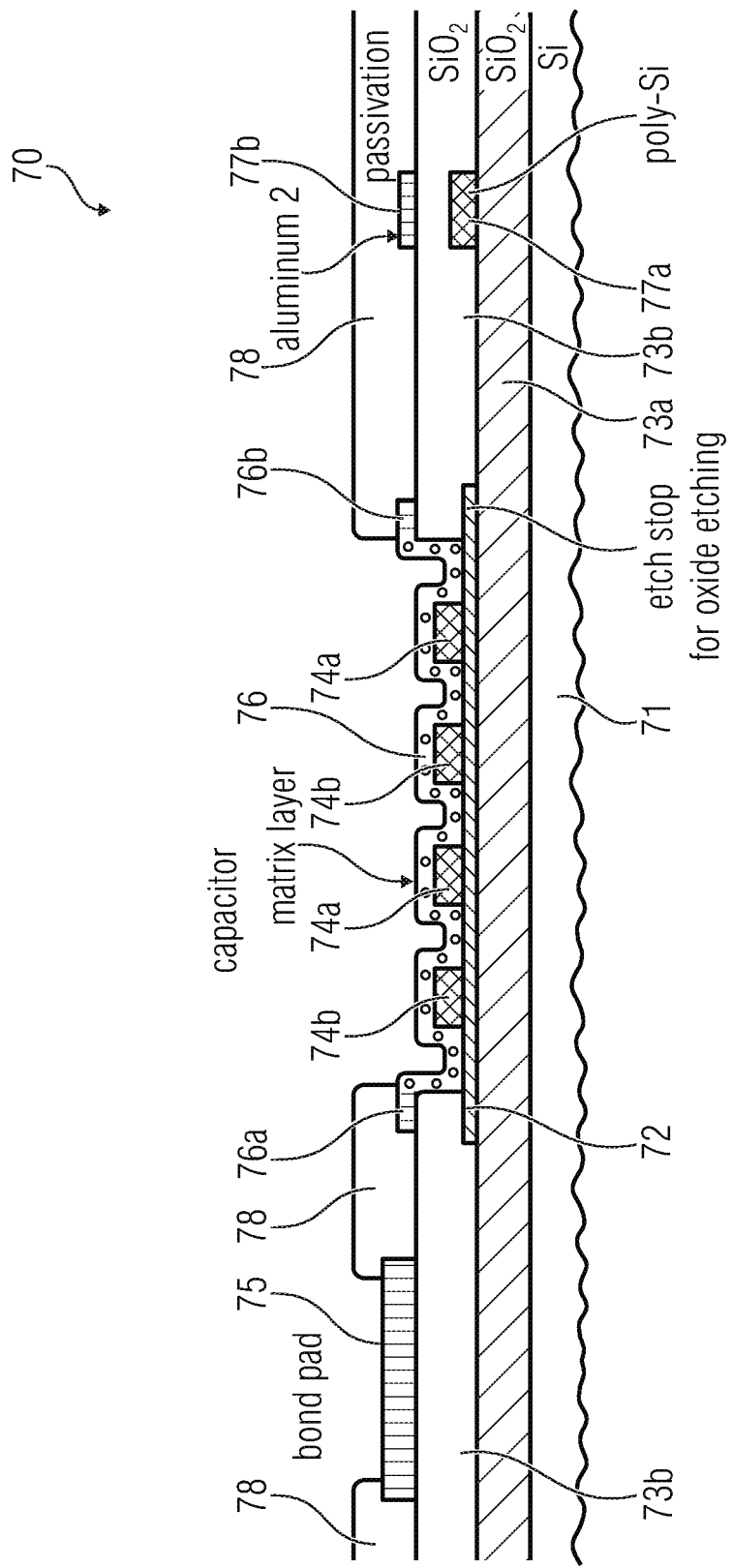

FIG. 7a shows a semiconductor device in accordance with embodiments of the invention, which implements an interdigital capacitor 70. The interdigital capacitor 70 is shown in a cross-sectional drawing in FIG. 7a, where one can see a layer build-up which is typical for a semiconductor manufacturing process. A silicon substrate 71 has a first insulating layer 73a made of silicon dioxide arranged thereon. The first insulating layer 73a has a portion having a second insulating layer 73b located thereon, followed by a portion having a silicon nitride layer 72, followed by a further portion of the insulating layer 73b. The portion of the nitride layer 72 has polysilicon conductor lines 74a and 74b implemented therein which serve as a first electrode 74a and as a second electrode 74b of the interdigital capacitor 70. A non-conducting porous matrix structure 76 (which is manufactured in the semiconductor circuit, which can be seen, in particular, in that a left-hand portion 76a of the layer 76 and a right-hand portion 76b of the layer 76 still consist of elementary aluminum since said portions were covered by passivation during treatment of the precursor substance) is applied onto and between the electrodes 74a and 74b. A first segment of the second insulating layer 73b has a contact point 75 arranged thereon which may serve to contact, e.g., the first electrode 74a or the second electrode 74b. In addition, a passivation layer 78 is applied onto the interdigital capacitor such that, advantageously, only the contact point 75 as well as the porous matrix structure 76 are exposed. The second insulating layer 73b as well as the passivation layer 78 have conductor lines 77a and 77b implemented therein which may be used for contacting a precursor substance so as to be able to produce the porous matrix structure 76 by means of anodic oxidation. FIG. 7b shows the interdigital capacitor 70 in a top view, the contact point 75a of the first electrode 74b being configured to be rectangular and being bordered by the passivation 78, it being possible for said contact point to be the contact point 75, for example. In addition, the contact point 75b for contacting the second electrode 74b is configured to be rectangular and is bordered by the passivation 78. Moreover, it can be seen that the porous matrix structure 76 extends across the conductor lines of the first electrode 74a and the conductor lines of the second electrode 74b in a planar manner. Additionally, the opening of the passivation 78 is rectangular in the area of the porous matrix structure 76. One of the conductor lines 77a or 77b which may be used for contacting the precursor substance of the porous matrix structure 76 has also been drawn in. The conductor line 77a or 77b advantageously leads to a wafer edge (not drawn in) (in the event of implementation on a wafer) and is advantageously used for contacting during an anodic oxidization process. In addition, the conductor line 77a or 77b may be removed in a later process step once the porous matrix structure 76 has been formed. Furthermore, FIGS. 7a and b describe integration of an aluminum-based matrix layer by using the example of an interdigital capacitor.

General aspects of capacitors in accordance with embodiments of the invention will be addressed below. In accordance with embodiments, the capacitor electrodes of an interdigital capacitor have a thin insulating layer applied thereto which, as compared to the other embodiments which have already been described, has a porous matrix structure applied thereto. Advantageously, the matrix consists of an insulator here. By changing a relative permittivity or by changing a polarization of a reactive coating (e.g. functionalization substance within the porous matrix structure), changes in a complex impedance may be verified.

A further aspect in accordance with the invention describes generation of stable reactive coatings for sensor applications without any restriction being imposed by process parameters. Moreover, aspects in accordance with the invention relate to sensor-technology applications (gas sensor technology, sensor technology in liquids).

Two embodiments of producing matrix layers and of subsequent functionalization with a sensor coating will be described below. Said layers may be employed as integral parts of semiconductor production processes.

Embodiment: Aluminum

Typically, photodiodes are produced in a manner that includes contact hole opening, followed by overall aluminum deposition with the thickness (typically 0.7 to 1.0 μm) that is typical of the contacting, followed by patterning of the aluminum. Once a photoresist has been removed and the usual cleaning sequences have been performed, aluminum having a thickness (0.1 to 10 μm, advantageously 300 nm) which is used for matrix layer formation is deposited once again. This is followed by further patterning of the aluminum, which contains both electrical contacts and matrix structures. The matrix structures are mutually connected in an electrically conducting manner and form a contiguous electrode, advantageously at the wafer edge. Once the photoresist layer has been removed and the cleaning sequences have been performed, a passivation layer, advantageously made of silicon oxide and/or silicon nitride, is deposited and patterned in a known manner by means of etching processes. The electric terminals as well as the matrix fields and the edge contact are exposed in the process. The wafer is introduced into an electrolyte solution which may contain the usual substances such as sulfuric or oxalic acid, for example, for improving conductivity. By selectively applying a voltage (5 V to 25 V, by means of which the pore size is adjusted, advantageously 9 V) to an edge contact of the wafer, the matrix fields will be selectively modified without subjecting further electric terminals to any change. As the cathode, the usual materials (e.g. platinum) are employed. Following the usual processing steps, the entire wafer is introduced into a functionalization solution. Subsequently, a compaction step may be performed, e.g. by using water or water vapor, for stabilizing a sensor layer.

Embodiment: Porous Silicon

An integrated circuit is manufactured in a typical manner. By means of resistors made of porous silicon and functionalized by means of appropriate materials, sensor signals may be generated. To suppress disturbance variables, bridge circuits, by means of which temperature effects, for example, may be minimized, are particularly suited. For manufacturing resistors from porous silicon, silicon nitride is deposited as a chemical stop layer. Said layer has conductive polycrystalline silicon deposited thereon. The grain size of the crystallites may be adjusted by means of the deposition temperature. Typically, layer thicknesses of 0.1 to 1 µm are deposited. Said layer thickness defines a matrix thickness of porous silicon. Further process steps include intermediate oxide deposition, contact hole etching, metallization, metal patterning and passivation. For producing the porous silicon layer, the polysilicon layer is now exposed by removing the intermediate oxide and the passivation layer. A protective layer of photoresist covers all other structures apart from the polysilicon layer to be processed. The wafer thus prepared is dipped into hydrofluoric acid and, as is also described under FIG. 1, contacted at the edge, and has a voltage applied to it. By means of said voltage, the polycrystalline silicon is anodically oxidized, and the resulting silicon dioxide is dissolved by using hydrofluoric acid. As a cathode, the usual materials are employed (e.g. platinum). A pore size may be adjusted by the voltage applied and by the crystallite size of the polysilicon. The photoresist is removed by means of a solvent which absorbs no water so as not to dehydrate the pores and thus not to contaminate them with residues of photoresist. Functionalization may now be performed in two ways. In a first variant, the porous Si is not dried but conditioned with suitable solvents which have the functionalization substances dissolved therein. In a second variant, the porous Si is dried in the known manner, so that the pores are preserved. Subsequently, the dissolved functionalization substances are applied. The subsequent drying procedure is dependent on the solvent. In the case of water, common drying methods such as overcritical drying or pentane drying, for example, may be employed.

If sealing of the pores should be useful, this may be performed, e.g., by means of water vapor or a plasma process.

Functionalization Substances

Functionalization substances may be sensor materials, for example. Such sensor materials react in a targeted manner with analytes, e.g. target gases, ions, neutral molecules with reactive groups, or to physical influences, and consequently change their properties. Said changes may relate to the chemical functionality and/or to physical properties. Said changes may be changes in the dipole moment, charge changes or other effects, which may then be evaluated, e.g., as optical properties (absorption, luminescence, refractive index) and/or electrical properties (conductance, work function).

Via the selection of a basic chemical backbone of the functionalization substance, the properties which have already been mentioned may be promoted, enhanced or even created. For example, changes in color (changes in the dipole moment), charge changes or further physical effects may be created which may be evaluated in an optical or electrical manner.

By incorporating functionalization substances into porous aluminum oxide or silicon, one may dispense with a fixation substance. Said type of fixation offers several advantages over known fixation methods, e.g. binding via anchor groups or embedding into polymer matrices. Binding via anchor groups may often be implemented only with considerable synthetic expenditure or is not at all possible. Fixation of functionalization substances by embedding them into polymer materials may possibly adversely affect the response behavior of the functionalization substances (e.g., diffusion of target gases may be impeded). In addition, aging of the polymer materials, which often involves their decomposition, may have an undesired influence on the functionalization substances.

By incorporating the functionalization substances into porous aluminum oxide or silicon, however, reaction with the analyte may occur without any interfering matrix influences.

To ensure entering of the functionalization substances into the pores, surfaces used are wettable for the respective substance group in order to enable maximum loading. If the untreated porous aluminum oxide or silicon turns out to be unsuitable, uptake of the porous aluminum oxide or silicon may be promoted by means of the usual surface functionalizations.

EXAMPLES

An example of a functional group (of a functionalization substance) is an amino group for detecting $CO_2$.

$$R-NH_{2(functional\ group)} + CO_{2(gas)} \rightarrow R-NHCOO^- + H^+$$

The amino group attached to the functionalization substance reacts with $CO_2$ to form a carbamic acid. Due to the acid formation, changes in the physical and chemical properties may be derived (such as a change in the pH value or electrical conductivity, for example).

Examples of Analytes (e.g. Fluids or Gases)

Volatile organic compounds such as those among the classes of substances of alkanes, alcohols, aldehydes, esters, ethers, ketones, carbonic acids, amines, nitro compounds (e.g. TNT)

Inorganic gases such as carbon dioxide, carbon monoxide, nitrogen dioxide, nitrogen oxides, sulfur dioxide, ammonia, hydrogen chloride.

Examples of Functionalization Substances

Triphenylmethane dyes, azo dyes, stilbene dyes, ORMOCER®s, quaternary ammonium compounds, porphyrins (metal complexes).

The functionalization substances described herein are mainly exemplary and are not meant to limit the protective scope to the functionalization substances mentioned.

Examples of Chemical Reactions

Oxidative or reductive reactions, acid/base reactions, ligand binding to active metal complexes Advantages of the inventive embodiments over conventional components will be discussed below.

Transistors

Direct application of the substances in thin layers at temperatures or by using methods which do not destroy the substances (vapor depositing of metals, sputtering, chemical vapor deposition (CVD)). Thus, there are only a small number of substances available, and only few analytes may be verified.

Resistors

Heated porous masses which are coated with platinum or the like and verify combustible gases in that a change in the resistance is caused. Said method is very unspecific. A further method uses nanotubes which are coated with indicator materials and also react to the presence of gases with changes in the resistance. There is a lack of methods which are suitable for mass production and ensure reliable contacting of the nanotubes.

Capacitors

Said capacitors come in two embodiments, namely interdigital capacitors and capacitors with porous electrodes, which are coated with dielectric indicator materials. Typically, only the change in air humidity is identified, which results in a change in capacitance. Integration into the manufacturing process of semiconductor components clearly limits the selection of suitable dielectric indicator layers since the process parameters specify framework conditions (e.g. the temperature) for which many, particularly organic, materials are not suitable.

Photodiodes

Photodiodes which are coated during the manufacturing process are only known as color detectors (cameras). Photodiodes comprising indicator layers applied during the process are currently not known.

The conventional solutions indicated above use extremely different methods and mostly cannot be integrated directly into a manufacturing process. Also, the indicator layers are not randomly modifiable after the process has ended.

The method introduced here may be readily introduced into a manufacturing process, and modification of the coating may be readily adapted to most varied requirements.

The respective component, such as transistor, resistor, capacitor and photoreceiver (photodiode) may be modified into sensor components by means of the same manufacturing method. To this end, a porous conducting or non-conducting layer, which serves as a matrix and which has a reactive coating immobilized therein, is introduced into the respective sensitive area (area to be sensitized) of the component. Said coating may also be produced once the component has been manufactured.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A semiconductor device comprising:
    a semiconductor substrate;
    wherein the semiconductor substrate comprises a plurality of integrated circuit configurations;
    wherein the integrated circuit configurations comprise a layer which includes a porous matrix structure,
    wherein a functionalization substance is introduced into the porous matrix structure,
    wherein the functionalization substance is a sensor material, and wherein the sensor material exhibits a property which depends on a state of a fluid which is in contact with the sensor material,
    wherein the integrated circuit configurations comprise an optically sensitive area, wherein the porous matrix structure is arranged in a direction of incident light of the optically sensitive area,
    wherein the sensor material is configured to influence an electric signal of the optically sensitive area on the basis of a state of the fluid, and wherein the semiconductor device is configured to sense a state of the fluid on the basis of the influence exerted on the electric signal, and
    wherein the optically sensitive area is configured to receive light through the porous matrix structure, wherein the light undergoes an absorption through the sensor material in the porous matrix structure on the basis of a state of the fluid.

2. The semiconductor device as claimed in claim 1, which has been manufactured in accordance with a method of producing a semiconductor device, said method comprising:
    providing a carrier structure comprising a semiconductor substrate;
    applying or introducing a precursor substance onto or into the carrier structure;
    treating the precursor substance for producing a porous matrix structure;
    introducing a functionalization substance into the porous matrix structure.

3. The semiconductor device as claimed in claim 1, wherein the layer comprising the porous matrix structure is integrated into the semiconductor device by means of a chemical bond without any adhesive.

4. The semiconductor device as claimed in claim 1, wherein the porous matrix structure is based on an electrically conducting material.

5. The semiconductor device as claimed in claim 1, wherein the porous matrix structure is based on an electrically insulating material.

6. The semiconductor device as claimed in claim 1, wherein the porous matrix structure is optically transparent.

7. The semiconductor device as claimed in claim 1, wherein the functionalization substance is based on a triphenylmethane dye, an azo dye, a stilbene dye, ORMOCER®s, a quaternary ammonium compound, or a metal complex.

8. The semiconductor device as claimed in claim 1, wherein the porous matrix structure is applied onto the semiconductor substrate, an oxide layer of the carrier structure, a nitride layer of the carrier structure, or a semiconductor layer of the carrier structure.

9. The semiconductor device as claimed in claim 1, wherein the porous matrix structure comprises aluminum oxide, quartz or porous silicon.

10. A semiconductor device structure comprising:
- a semiconductor substrate;
- wherein the semiconductor substrate comprises a plurality of integrated circuit configurations;
- wherein the integrated circuit configurations comprise a layer which includes a porous matrix structure,
- wherein a functionalization substance is introduced into the porous matrix,
- wherein the functionalization substance is a sensor material, and wherein the sensor material exhibits a property which depends on a state of a fluid which is in contact with the sensor material,
- wherein the integrated circuit configurations comprise an optically sensitive area, wherein the porous matrix structure is arranged in a direction of incident light of the optically sensitive area, and
- wherein the sensor material is configured to influence an electric signal of the optically sensitive area on the basis of a state of the fluid, and wherein the semiconductor device is configured to sense a state of the fluid on the basis of the influence exerted on the electric signal, and
- wherein the optically sensitive area is configured to receive light, the light undergoing a refraction within the porous matrix structure on the basis of a state of the fluid, and the semiconductor device being configured to sense the state or a state of the fluid on the basis of said refraction.

11. A semiconductor device comprising:
- a semiconductor substrate;
- wherein the semiconductor substrate comprises a plurality of integrated circuit configurations;
- wherein the integrated circuit configurations comprise a layer which includes a porous matrix structure,
- wherein a functionalization substance is introduced into the porous matrix structure,
- wherein the functionalization substance is configured to perform bonding with a further porous matrix structure, said further porous matrix structure being loaded with the functionalization substance.

* * * * *